(12) United States Patent
Morita

(10) Patent No.: US 12,036,062 B2
(45) Date of Patent: Jul. 16, 2024

(54) NEAR FIELD COMMUNICATION SYSTEM, X-RAY CT APPARATUS, AND NEAR FIELD COMMUNICATION CONTROLLING METHOD

(71) Applicant: CANON MEDICAL SYSTEMS CORPORATION, Tochigi (JP)

(72) Inventor: Jun Morita, Bunkyo-ku (JP)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 287 days.

(21) Appl. No.: 17/658,545

(22) Filed: Apr. 8, 2022

(65) Prior Publication Data
US 2022/0323038 A1    Oct. 13, 2022

(30) Foreign Application Priority Data
Apr. 8, 2021   (JP) ................. 2021-066030

(51) Int. Cl.
*A61B 6/03*    (2006.01)
*A61B 6/00*    (2006.01)
*H04B 5/24*    (2024.01)
*H04B 5/70*    (2024.01)

(52) U.S. Cl.
CPC ............ *A61B 6/56* (2013.01); *A61B 6/032* (2013.01); *A61B 6/4435* (2013.01); *H04B 5/24* (2024.01); *H04B 5/70* (2024.01)

(58) Field of Classification Search
CPC .... A61B 6/00; A61B 6/03; A61B 6/56; A61B 6/032; A61B 6/4435; A61B 6/4233; A61B 6/585; A61B 6/4241; H04B 5/00; H04B 5/0075; H04B 5/0025; H04B 5/24; H04B 5/70; Y02D 30/70
See application file for complete search history.

(56) References Cited

U.S. PATENT DOCUMENTS

2017/0085825 A1    3/2017   Okawa et al.

FOREIGN PATENT DOCUMENTS

| EP | 2 932 901 A1 | 10/2015 |
|---|---|---|
| JP | 2015-202415 A | 11/2015 |
| WO | WO 2007/004428 A1 | 1/2007 |
| WO | WO 2016/088421 A1 | 6/2016 |

*Primary Examiner* — Jurie Yun
(74) *Attorney, Agent, or Firm* — Oblon, McClelland, Maier & Neustadt, L.L.P.

(57) ABSTRACT

A near field communication system according to an embodiment includes: a long coupler provided for a first device; a short coupler provided for a second device and configured to perform wireless communication based on electromagnetic field coupling, with the long coupler; and signal processing circuitry configured to vary gain for each of various frequencies of a signal transmitted and received between the long coupler and the short coupler, in accordance with the position of the short coupler with respect to the long coupler.

20 Claims, 14 Drawing Sheets

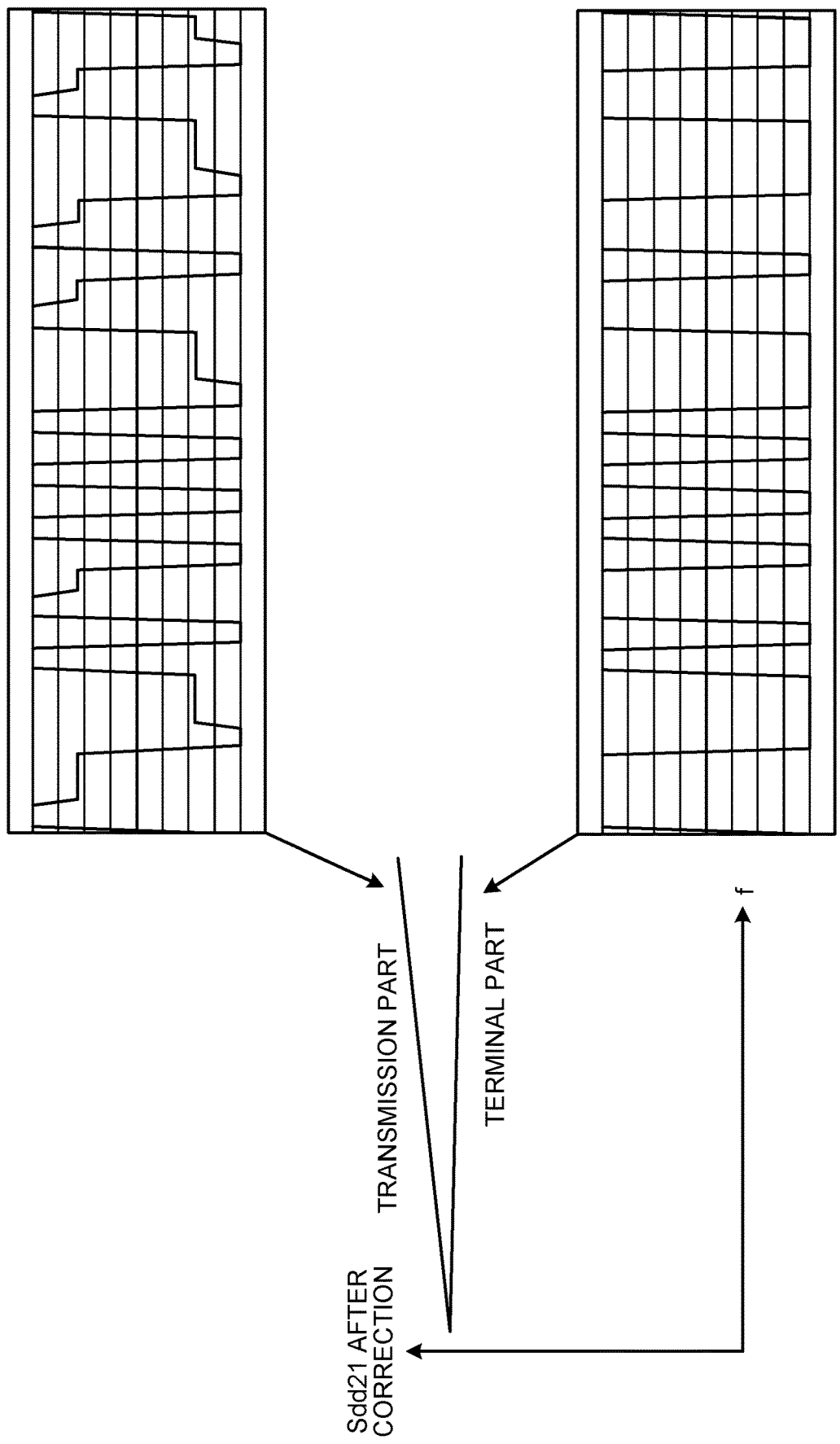

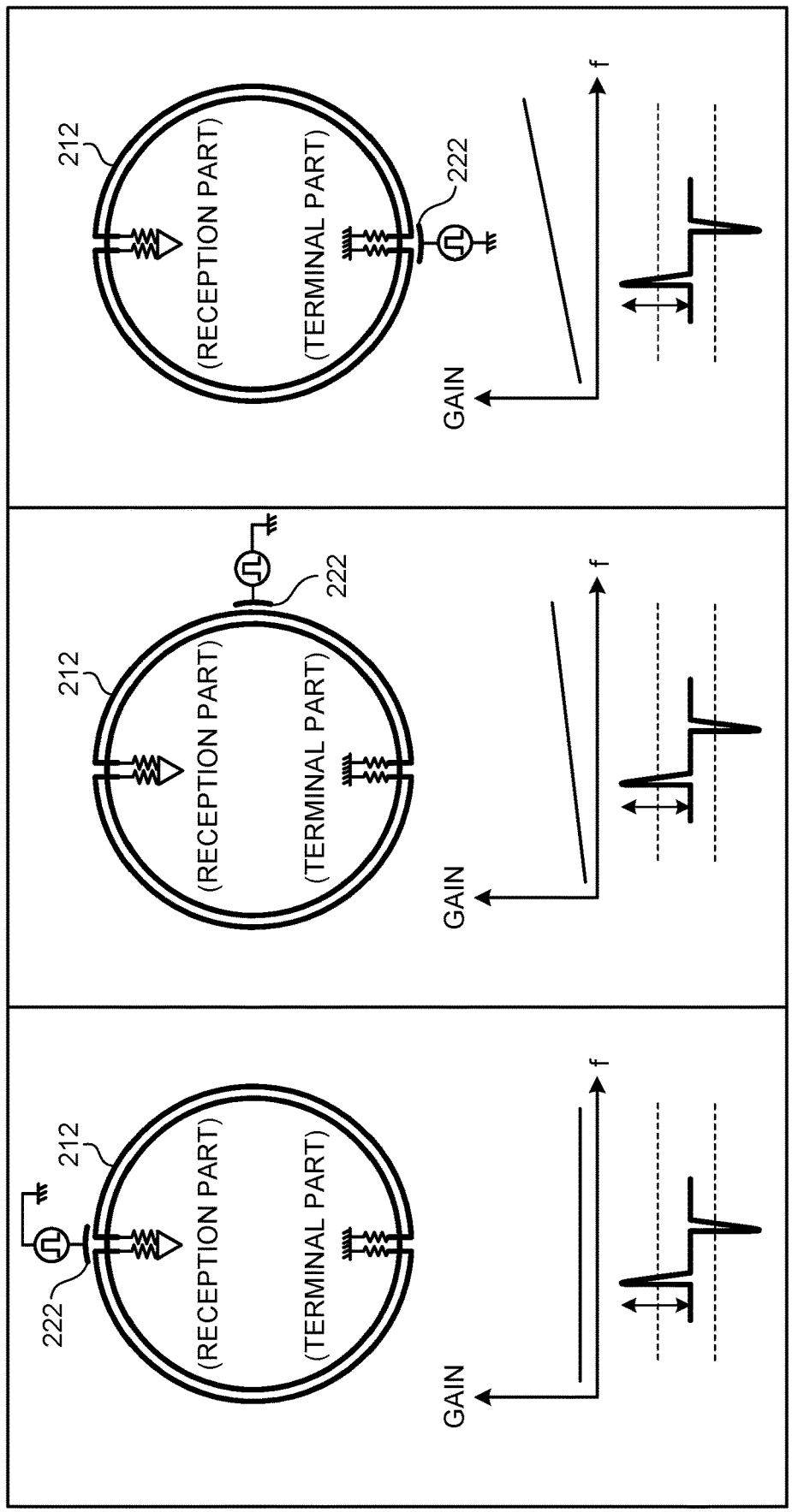

NEAR FIELD COMMUNICATION SYSTEM, X-RAY CT APPARATUS, AND NEAR FIELD COMMUNICATION CONTROLLING METHOD

CROSS-REFERENCE TO RELATED APPLICATIONS

This application is based upon and claims the benefit of priority from Japanese Patent Application No. 2021-066030, filed on Apr. 8, 2021; the entire contents of which are incorporated herein by reference.

FIELD

Embodiments described herein relate generally to a near field communication system, an X-ray Computed Tomography (CT) apparatus, and a near field communication controlling method.

BACKGROUND

Wireless communication techniques based on electromagnetic field coupling are known. According to one of these techniques, a signal is transmitted and received between a pair of communication circuits (which may be called "couplers") coupled by electromagnetic field coupling. For example, in an X-ray Computed Tomography (CT) apparatus, X-rays are detected in a rotating part that rotates around an examined subject, so that a result of the X-ray detection is wirelessly transmitted from the rotating part to a fixed part. To the transmission of the result of the X-ray detection, it is possible to apply the wireless communication technique based on the electromagnetic field coupling.

BRIEF DESCRIPTION OF THE DRAWINGS

FIG. 10B is a drawing illustrating waveforms resulting from the correcting process according to the first embodiment;

FIG. 17 is a drawing illustrating waveforms that have been corrected while gain is varied by signal processing units according to the second embodiment, in the situation where the shaping circuitry in FIG. 4A is applied.

DETAILED DESCRIPTION

In the following sections, exemplary embodiments of a near field communication system, an X-ray CT apparatus, and a near field communication controlling method will be explained in detail, with reference to the accompanying drawings.

Figure 1:
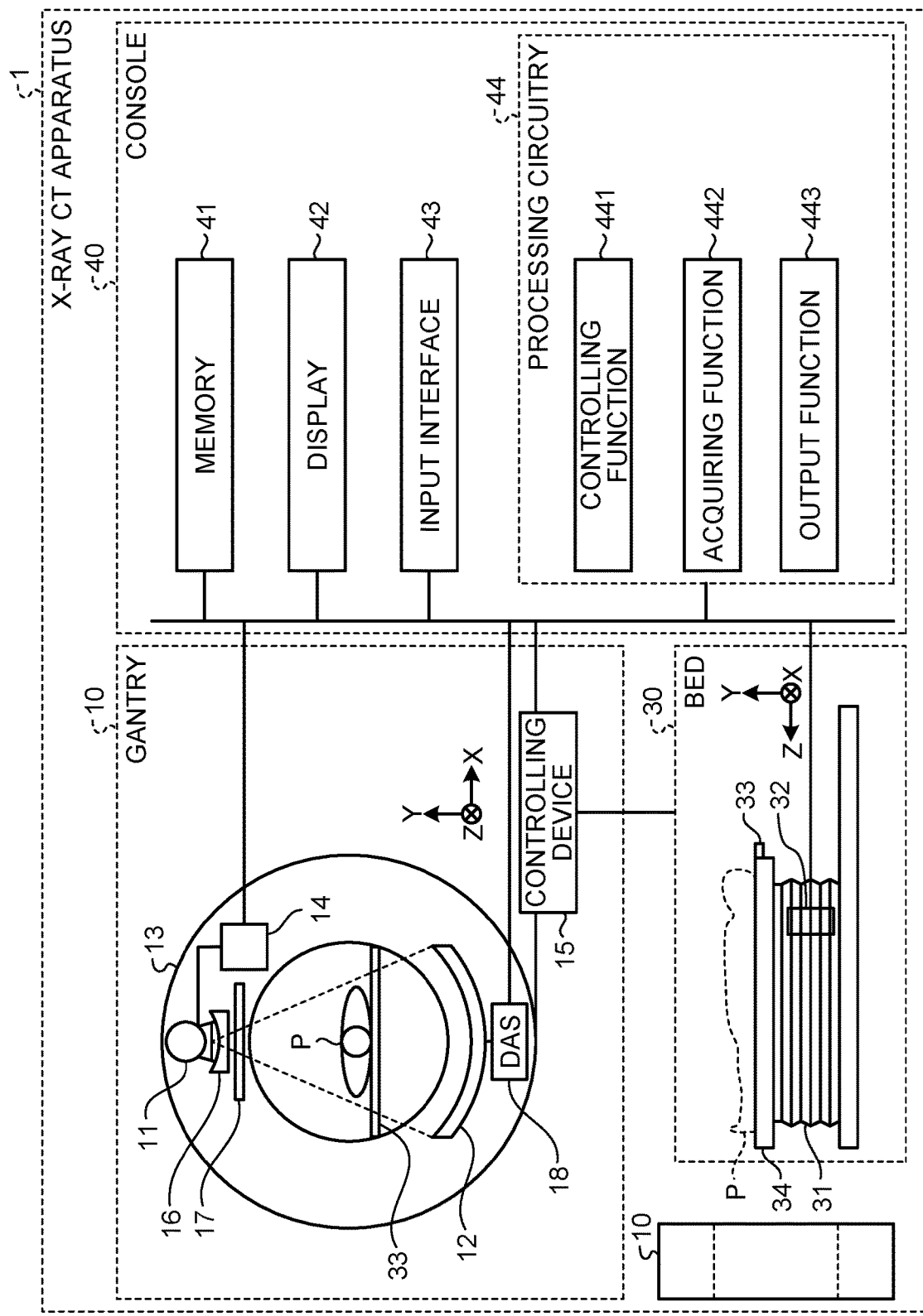
FIG. 1 is a block diagram illustrating an exemplary configuration of an X-ray CT apparatus according to a first embodiment.

The following will describe an example of an X-ray CT apparatus 1 including a near field communication system 20. FIG. 1 is a block diagram illustrating an exemplary configuration of the X-ray CT apparatus 1 according to a first embodiment. For example, the X-ray CT apparatus 1 includes a gantry 10, a bed 30, and a console 40.

In FIG. 1, a rotation axis of a rotating frame 13 in a non-tilt state or the longitudinal direction of a tabletop 33 of the bed 30 is defined as a Z-axis direction. Further, the axial direction orthogonal to the Z-axis direction and parallel to a floor surface is defined as an X-axis direction. Also, the axial direction orthogonal to the Z-axis direction and perpendicular to the floor surface is defined as a Y-axis direction. Although FIG. 1 depicts the gantry 10 from multiple directions for the sake of convenience in the explanation, the X-ray CT apparatus 1 includes the single gantry 10.

The gantry 10 includes an X-ray tube 11, an X-ray detector 12, the rotating frame 13, an X-ray high-voltage device 14, a controlling device 15, a wedge 16, a collimator 17, and a Data Acquisition System (DAS) 18. Also, the gantry 10 further includes the near field communication system 20 (not illustrated). The near field communication system 20 will be explained later.

The X-ray tube 11 is a vacuum tube including a negative pole (a filament) configured to generate thermo electrons and a positive pole (a target) configured to generate X-rays upon collisions of the thermo electrons. The X-ray tube 11 is configured to generate X-rays to be radiated onto an examined subject (hereinafter, "patient") P, by causing the thermo electrons to be emitted from the negative pole toward the positive pole, by applying high voltage supplied from the X-ray high-voltage device 14. The X-ray tube 11 is an example of the X-ray generating unit.

The X-ray detector 12 is configured to detect X-rays that were radiated from the X-ray tube 11 and have passed through the patient P and is configured to output a signal corresponding to the amount of detected X-rays to the DAS 18. The X-ray detector 12 includes, for example, a plurality of rows of detecting elements in each of which a plurality of detecting elements are arranged in a channel direction along an arc centered on a focal point of the X-ray tube 11. For example, the X-ray detector 12 has a structure in which the plurality of rows each having a plurality of detecting elements disposed in the channel direction are arranged in a row direction (a slice direction). The X-ray detector 12 is an example of the X-ray detecting unit.

For example, the X-ray detector 12 is a detector of an indirect-conversion type including a grid, a scintillator array, and an optical sensor array. The scintillator array includes a plurality of scintillators. The scintillators each include a scintillator crystal that outputs light in a photon quantity corresponding to the amount of X-rays becoming incident thereto. The grid is arranged on a surface of the scintillator array that is positioned on the X-ray incident side and includes an X-ray blocking plate to absorb scattered X-rays. The grid may be referred to as a collimator (a one-dimensional collimator or a two-dimensional collimator) in some situations. The optical sensor array has a function of converting the light from the scintillators into an electrical signal corresponding to the quantity of light and includes optical sensors such as photodiodes, for example. Alternatively, the X-ray detector 12 may be a detector of a direct-conversion type including a semiconductor element configured to convert X-rays having become incident thereto into an electrical signal.

The rotating frame 13 is an annular frame configured to support the X-ray tube 11 and the X-ray detector 12 so as to oppose each other and configured to rotate the X-ray tube 11 and the X-ray detector 12 via the controlling device 15 (explained later). For example, the rotating frame 13 is a cast product using aluminum as a material thereof. In addition to the X-ray tube 11 and the X-ray detector 12, the rotating frame 13 may further support the X-ray high-voltage device 14, the wedge 16, the collimator 17, the DAS 18, and/or the like. Additionally, the rotating frame 13 may further support various elements that are not illustrated in FIG. 1. For example, the rotating frame 13 may support a rotating-part side communication unit 21 (explained later).

In the following sections, in the gantry 10, the rotating frame 13 and a part that makes a rotating movement together with the rotating frame 13 may be referred to as a rotating part (a rotor). The rotating part is an example of the first device and is configured to be rotatable around the patient P. The rotating part includes, for example, the rotating frame 13, the X-ray tube 11, the X-ray detector 12, and the rotating-part side communication unit 21. In contrast, in the following sections, a part in the gantry 10 that supports the rotating part but does not rotate may be referred to as a fixed part (a stator). The fixed part includes a fixed-part side communication unit 22 (explained later) and a rotating mechanism to cause the rotating frame 13 to rotate. In other words, the rotating frame 13 is rotatably supported by the fixed part. For example, the rotating mechanism includes a motor configured to generate a rotation drive force and a bearing configured to transmit the rotation drive force to the rotating frame 13 to cause the rotation. For example, the motor is provided in the fixed part. The bearing is physically connected to the rotating frame 13 and the motor. The rotating frame rotates in accordance with a rotating force of the motor.

The X-ray high-voltage device 14 includes: a high-voltage generating device including electric circuitry such as a transformer and a rectifier and being configured to generate the high voltage to be applied to the X-ray tube 11; and an X-ray controlling device being configured to control output voltage in accordance with the X-rays generated by the X-ray tube 11. The high-voltage generating device may be of a transformer type or an inverter type. Further, the X-ray high-voltage device 14 may be included in the rotating part or may be included in the fixed part.

The controlling device 15 includes processing circuitry including a Central Processing Unit (CPU) or the like and a driving mechanism such as a motor and an actuator. The controlling device 15 is configured to control operations of the gantry 10 and the bed 30, by receiving input signals from the input interface 43. For example, the controlling device 15 is configured to exercise control over the rotation of the rotating frame 13, tilting of the gantry 10, operations of the bed 30, and the like. In one example, as the control to tilt the gantry 10, the controlling device 15 is configured to rotate the rotating frame 13 on an axis parallel to the X-axis direction, according to inclination angle (tilt angle) information being input. The controlling device 15 may be provided for the gantry 10 or may be provided for the console 40.

The wedge 16 is an X-ray filter used for adjusting the amount of X-rays radiated from the X-ray tube 11. More specifically, the wedge 16 is an X-ray filter configured to attenuate the X-rays radiated from the X-ray tube 11 so that the X-rays radiated from the X-ray tube 11 onto the patient P has a predetermined distribution. For example, the wedge 16 may be a wedge filter or a bow-tie filter and is manufactured by processing aluminum or the like so as to have a predetermined target angle and a predetermined thickness.

The collimator 17 is realized with lead plates or the like for narrowing down an emission range of the X-rays that have passed through the wedge 16 and is configured to form a slit by combining together the plurality of lead plates or the like. The collimator 17 may be referred to as an X-ray limiter. Further, although FIG. 1 illustrates the example in which the wedge 16 is provided between the X-ray tube 11 and the collimator 17, the collimator 17 may be provided between the X-ray tube 11 and the wedge 16. In that situation, the wedge 16 is configured to pass and attenuate the X-rays which are radiated from the X-ray tube 11 and of which the emission range is limited by the collimator 17.

The DAS 18 is configured to acquire a signal of the X-rays detected by the detecting elements included in the X-ray detector 12. For example, the DAS 18 includes an amplifier that performs an amplifying process on the electrical signal output from the detecting elements; and an Analog/Digital (A/D) converter that converts the electrical signal into a digital signal and is configured to generate detection data. For example, the DAS 18 is realized by using a processor. The data generated by the DAS 18 is transmitted to the fixed part by using a wireless communication technique based on electromagnetic field coupling. This feature will be explained later.

The bed 30 is a device on which the patient P undergoing a CT scan is placed and which is configured to move the patient P. The bed 30 includes a base 31, a table driving device 32, the tabletop 33, and a supporting frame 34. The base 31 is a casing configured to support the supporting frame 34 so as to be movable in vertical directions. The table driving device 32 is a driving mechanism configured to move the tabletop 33 on which the patient P is placed in the long-axis direction of the tabletop 33 and includes a motor and an actuator or the like. The tabletop 33 provided on the top face of the supporting frame 34 is a board on which the patient P is placed. The table driving device 32 may also be configured to move, in addition to the tabletop 33, the supporting frame 34 in the long-axis direction of the tabletop 33.

The console 40 includes a memory 41, a display 42, an input interface 43, and processing circuitry 44. In the present example, the console 40 and the gantry 10 are described as separate devices. However, the gantry 10 may include the console 40 or one or more of the constituent elements of the console 40.

For example, the memory 41 is realized by using a semiconductor memory element such as a Random Access Memory (RAM) or a flash memory, or a hard disk, an optical disk, or the like. For example, the memory 41 is configured to save therein various types of data acquired from the patient P and to store therein a program for enabling the circuitry included in the X-ray CT apparatus 1 to realize the functions thereof.

The display 42 is, for example, a liquid crystal display or a Cathode Ray Tube (CRT) display. For example, the display 42 is configured to display an X-ray CT image acquired from the patient P and a Graphical User Interface (GUI) used for receiving various types of instructions, settings, and the like from a user. The display 42 may be of a desktop type or may be configured by using a tablet terminal or the like capable of wirelessly communicating with the main body of the X-ray CT apparatus 1. Alternatively, the X-ray CT apparatus 1 may be provided with a projector in place of or in addition to the display 42. Under control of the processing circuitry 44, the projector is configured to project images on a screen, a wall, a floor, the body surface of the patient P, or the like. In one example, the projector is able to project images on an arbitrary plane, object, space, or the like through a projection mapping process.

The input interface 43 is configured to receive various types of input operations from the user, to convert the received input operations into electrical signals, and to output the electrical signals to the processing circuitry 44. For example, the input interface 43 is realized by using a mouse, a keyboard, a trackball, a switch, a button, a joystick, a touchpad on which input operations can be performed by touching an operation surface thereof, a touch screen in which a display screen and a touchpad are integrally formed, contactless input circuitry using an optical sensor, audio input circuitry, and/or the like. In this situation, the input interface 43 may be configured by using a tablet terminal or the like capable of wirelessly communicating with the main body of the X-ray CT apparatus 1. Further, the input interface 43 may be circuitry configured to receive input operations from the user via motion capture. In one example, the input interface 43 is capable of receiving body movements, lines of sight, and the like of the user as input operations, by processing signals obtained via a tracker and images acquired of the user. Further, the input interface 43 does not necessarily have to include physical operation component parts such as a mouse, a keyboard, and/or the like. For instance, possible examples of the input interface 43 include electrical signal processing circuitry configured to receive an electrical signal corresponding to an input operation from an external input device provided separately from the X-ray CT apparatus 1 and to output the electrical signal to the processing circuitry 44.

The processing circuitry 44 is configured to control operations of the entirety of the X-ray CT apparatus 1, by executing a controlling function 441, an acquiring function 442, and an output function 443.

For example, by reading and executing a program corresponding to the controlling function 441 from the memory 41, the processing circuitry 44 is configured to control various types of functions such as the acquiring function 442 and the output function 443, on the basis of the various types of input operations received from the user via the input interface 43.

Further, for example, by reading and executing a program corresponding to the acquiring function 442 from the memory 41, the processing circuitry 44 is configured to perform the CT scan on the patient P. For example, by controlling the X-ray high-voltage device 14, the acquiring function 442 is configured to supply the high voltage to the X-ray tube 11. Accordingly, the X-ray tube 11 is configured to generate the X-rays to be radiated onto the patient P. Further, by controlling the table driving device 32, the acquiring function 442 is configured to move the patient P into an image taking opening of the gantry 10. Further, by adjusting the position of the wedge 16 and an opening degree and the position of the collimator 17, the acquiring function 442 is configured to control a distribution of the X-rays radiated onto the patient P. Further, by controlling the controlling device 15, the acquiring function 442 is configured to cause the rotating part to rotate. Furthermore, while the CT scan is performed by the acquiring function 442, the DAS 18 is configured to acquire the signal of the X-rays from the detecting elements included in the X-ray detector 12 and to generate the detection data.

The detection data generated by the DAS 18 is transmitted from the rotating part to the fixed part. More specifically, the detection data is wirelessly transmitted from the rotating-part side communication unit 21 included in the rotating part, to the fixed-part side communication unit 22 included in the fixed part, so as to be further transmitted to the processing circuitry 44.

The acquiring function 442 is capable of performing a pre-processing process on the detection data received via the rotating-part side communication unit 21 and the fixed-part side communication unit 22. For example, on the detection data, the acquiring function 442 is configured to perform the pre-processing process such as a logarithmic conversion process, an offset correction process, an inter-channel sensitivity correction process, a beam hardening correction, and/or the like. Further, the data resulting from the pre-processing process may be referred to as raw data. Furthermore, the detection data prior to the pre-processing process and the raw data resulting from the pre-processing process may collectively be referred to as projection data. In addition, the acquiring function 442 is also capable of generating CT image data (volume data) on the basis of the projection data. For example, the acquiring function 442 is configured to generate the CT image data by performing a reconstruction process using a filtered backprojection method or a successive approximation reconstruction method, on the projection data resulting from the pre-processing process.

Further, for example, by reading and executing a program corresponding to the output function 443 from the memory 41, the processing circuitry 44 is configured to output various types of data. For example, the output function 443 is configured to control display processes of the display 42. For example, on the basis of an input operation received from the user via the input interface 43, the output function 443 is configured to convert the CT image data into a display-purpose image such as an arbitrary cross-sectional image or a rendering image from an arbitrary viewpoint direction and to cause the display 42 to display the display-purpose image.

Further, for example, the output function 443 is configured to transmit various types of data acquired by performing the CT scan on the patient P, to an external device via a network. For example, the output function 443 is configured to transmit and save the projection data and the CT image data described above into an image storage device (not illustrated). Examples of the image storage device include a server of a Picture Archiving and Communication System (PACS), for instance.

In the X-ray CT apparatus 1 illustrated in FIG. 1, the processing functions are stored in the memory 41 in the form of computer-executable programs. The processing circuitry 44 is a processor configured to realize the functions corresponding to the programs by reading and executing the programs from the memory 41. In other words, the processing circuitry 44 that has read the programs has the functions corresponding to the read programs.

Further, although the example was explained with reference to FIG. 1 in which the single processing circuit (i.e., the processing circuitry 44) realizes the controlling function 441, the acquiring function 442, and the output function 443; however, it is also acceptable to structure the processing circuitry 44 by combining together a plurality of independent processors, so that the functions are realized as a result of the processors executing the programs. Further, the processing functions of the processing circuitry 44 may be realized as being distributed among or integrated into one or more processing circuits, as appropriate.

Alternatively, the processing circuitry 44 may be configured to realize the functions by using a processor of an external device connected via a network. For example, the processing circuitry 44 may be configured to realize the functions illustrated in FIG. 1 by reading and executing the programs corresponding to the functions from the memory 41, while using a group of servers (a cloud) connected to the X-ray CT apparatus 1 via the network as computational resources.

Figure 2:
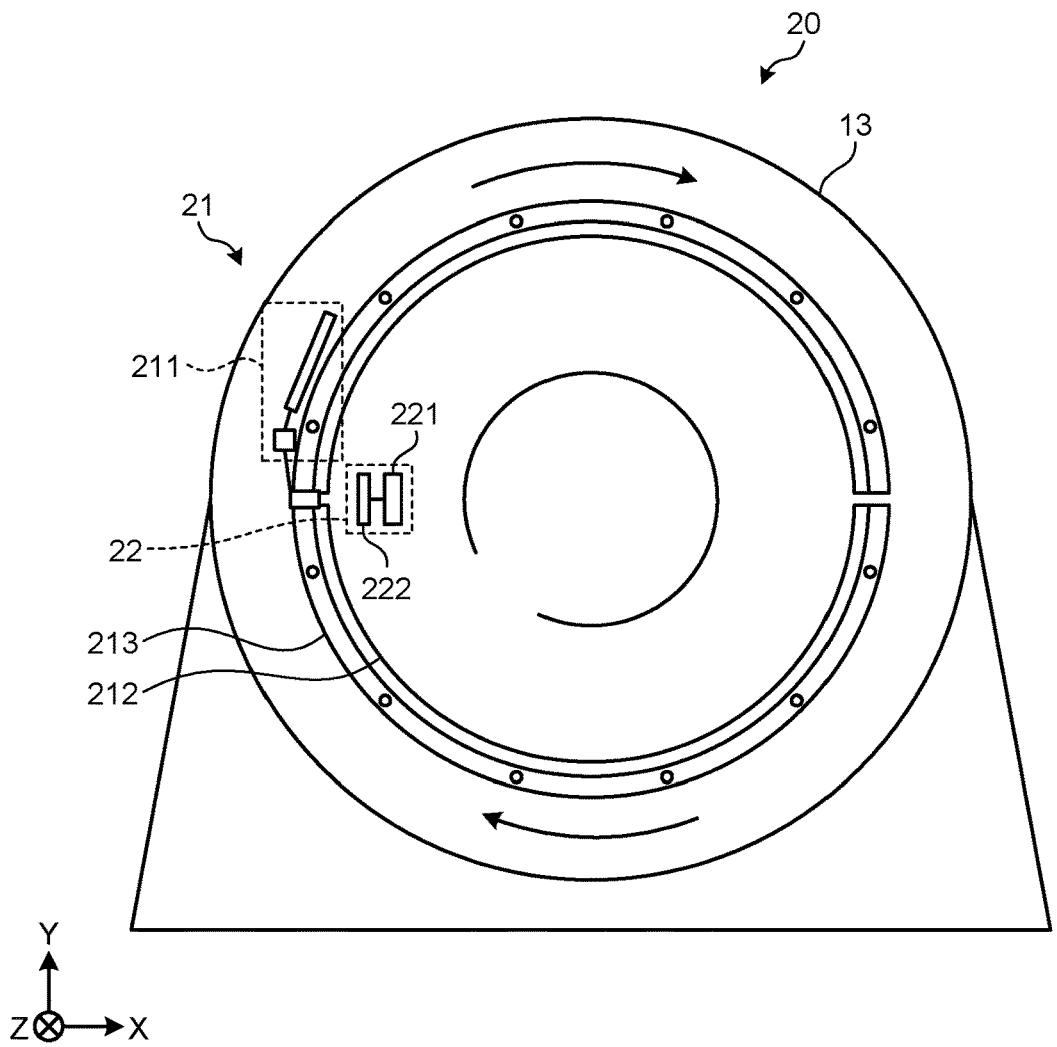
FIG. 2 is a block diagram illustrating an exemplary configuration of a near field communication system according to the first embodiment.

Next, the near field communication system 20 configured to perform the wireless communication between the rotating part and the fixed part will be explained, with reference to FIG. 2. FIG. 2 is a block diagram illustrating an exemplary configuration of the near field communication system 20 according to the first embodiment.

The near field communication system 20 includes the rotating-part side communication unit 21 and the fixed-part side communication unit 22. For example, the rotating-part side communication unit 21 includes a first signal processing unit 211, long couplers 212, and a jig 213. The rotating-part side communication unit 21 is provided for the rotating frame 13 and is configured, during a CT scan, to rotate around the patient P, together with the rotating frame 13. In other words, the rotating-part side communication unit 21 is included in the rotating part. Further, fixed-part side communication unit 22 includes a second signal processing unit 221 and a short coupler 222. The fixed-part side communication unit 22 is included in the fixed part.

The first signal processing unit 211 and the second signal processing unit 221 are each processing circuitry configured to perform various types of processes described below in relation to transmission or reception of signals. The first signal processing unit 211 may be referred to as first signal processing circuitry. The second signal processing unit 221 may be referred to as second signal processing circuitry. Also, when not being particularly distinguished from each other, the first signal processing circuitry and the second signal processing circuitry may simply be referred to as signal processing circuitry. The long couplers 212 and the short coupler 222 are a pair of communication circuitry coupled by electromagnetic field coupling. Further, as illustrated in FIG. 2, the dimension of the short coupler 222 in the circumferential direction of the rotating part is shorter than that of the long couplers 212. Further, the jig 213 is a ring-shaped member manufactured by using aluminum or the like. For example, when the long couplers 212 are Flexible Printed Circuits (FPCs), the jig 213 is able to fix the positions and the shapes of the long couplers 212 with respect to the rotating frame 13.

FIG. 2 illustrates the example in which the short coupler 222 is positioned inside, in terms of the radial direction, of the long couplers 212 that are circular; however, the position of the short coupler 222 with respect to the long couplers 212 is not particularly limited. For example, the short coupler 222 may be positioned outside, in terms of the radial direction, of the long couplers 212. In another example, the short coupler 222 may be provided in a position that is the same in terms of the radial direction and is different in terms of the Z direction, with respect to the long couplers 212.

Figure 3:
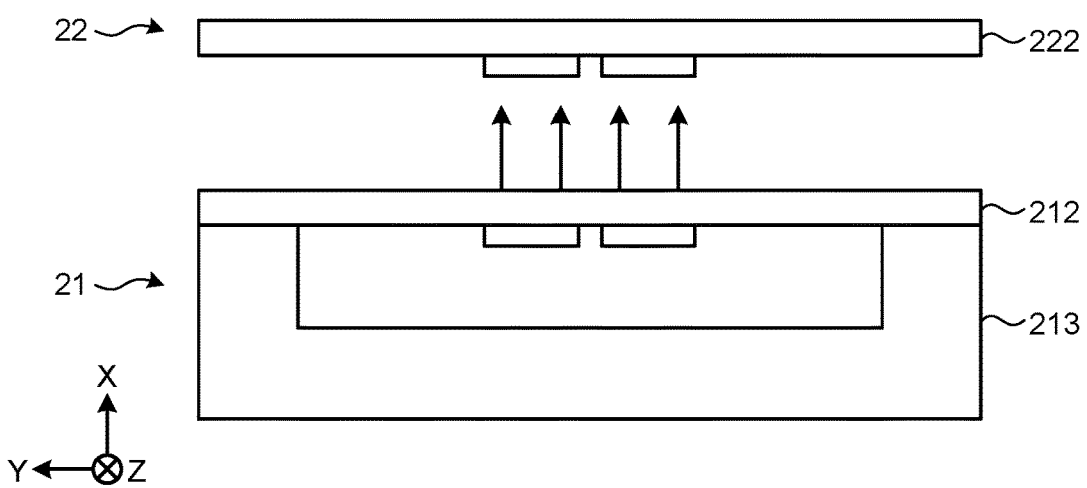
FIG. 3 is a diagram illustrating examples of cross-sectional structures of a long coupler and a short coupler according to the first embodiment.

FIG. 3 is a diagram illustrating examples of cross-sectional structures of a long coupler 212 and the short coupler 222 according to the first embodiment. As illustrated in FIG. 3, while facing each other without being in contact with each other, the long coupler 212 and the short coupler 222 structure the pair of communication circuitry coupled by the electromagnetic field coupling. In the present embodiment, an example will be explained in which a signal is transmitted from the long coupler 212 to the short coupler 222. In other words, in the present embodiment, it is assumed that the long coupler 212 is a transmission coupler, whereas the short coupler 222 is a reception coupler.

The exemplary configuration of the X-ray CT apparatus 1 including the near field communication system 20 has thus been explained. The near field communication system 20 structured as described above is configured to perform the wireless communication based on the electromagnetic field coupling, between the rotating part and the fixed part of the X-ray CT apparatus 1.

Figure 4A:
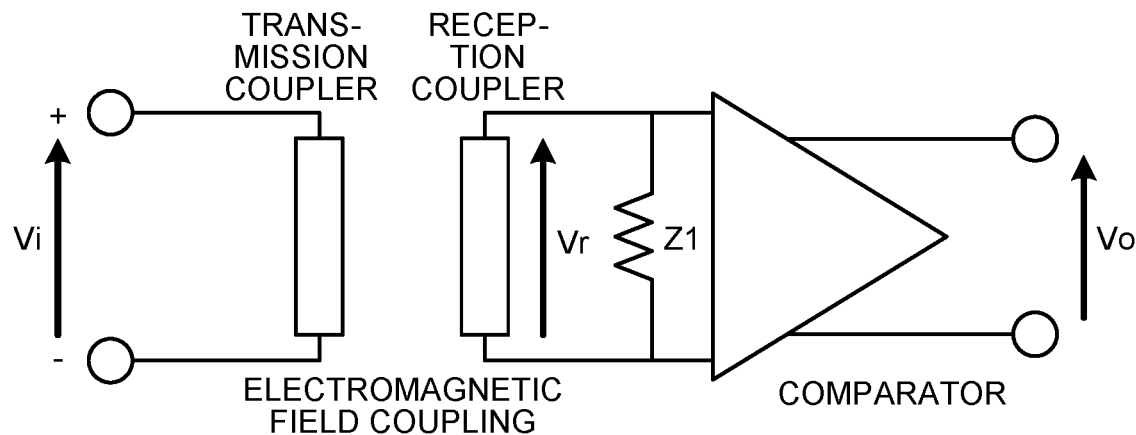
FIG. 4A is a diagram illustrating an example of shaping circuitry according to the first embodiment.

In this regard, in wireless communication based on electromagnetic field coupling, shaping circuitry may be used in some situations, in order to address signal attenuation, external noise, and the like that may be caused at the time of the communication. FIG. 4A is a diagram illustrating an example of shaping circuitry according to the first embodiment. In FIG. 4A, a transmission coupler and a reception coupler are coupled by electromagnetic field coupling, so that an input signal Vi is input from the transmission coupler side, and a reception signal Vr is received on the reception coupler side.

Figure 4B:
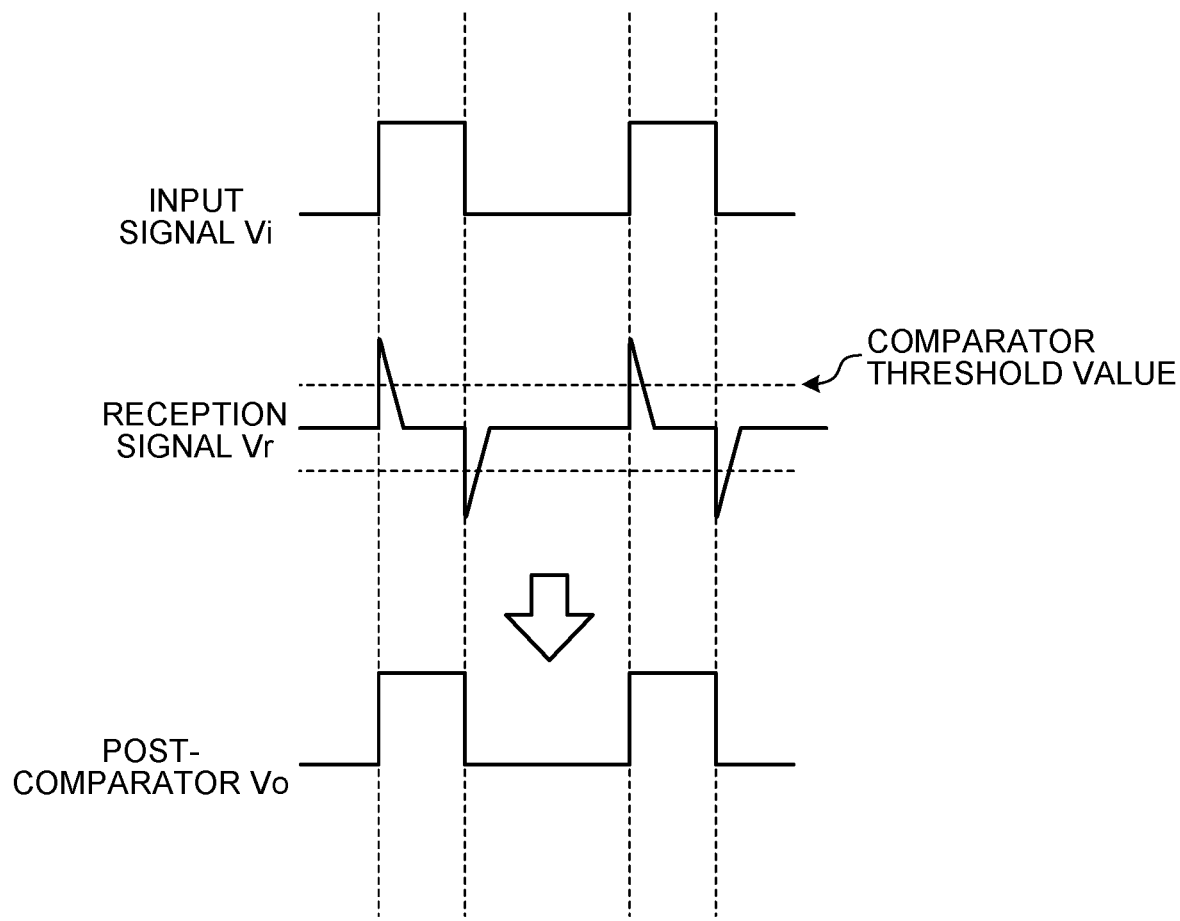
FIG. 4B is a chart illustrating an example of a waveform shaping process according to the first embodiment.

The shaping circuitry in FIG. 4A includes a comparator and also has relatively low impedance Z1. For example, the shaping circuitry in FIG. 4A is connected to the reception coupler and has a termination resistance of approximately 100Ω. In this situation, as illustrated in FIG. 4B, when the input signal Vi has a square wave, the reception signal Vr has a waveform reacting to edges of the input signal Vi. In other words, the reception signal Vr has the waveform indicating a high frequency component of the input signal Vi. The reception signal Vr is shaped so as to have a post-comparator waveform Vo illustrated in FIG. 4B. For example, the comparator is configured to convert the reception signal Vr into a square wave exhibiting the waveform Vo depicted in FIG. 4B, by outputting either "1" or "0" depending on whether or not the reception signal Vr exceeds a comparator threshold value. FIG. 4B is a chart illustrating the example of the waveform shaping process according to the first embodiment.

Figure 5A:
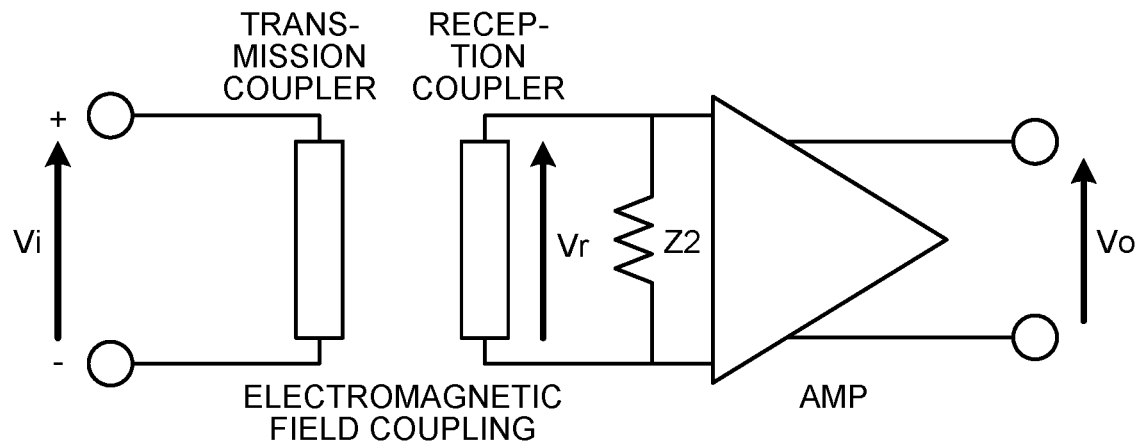
FIG. 5A is a diagram illustrating another example of shaping circuitry according to the first embodiment.

FIG. 5A is a diagram illustrating another example of shaping circuitry according to the first embodiment. Similarly to FIG. 4A, in FIG. 5A, a transmission coupler and a reception coupler are coupled by electromagnetic field coupling, so that the input signal Vi is input from the transmission coupler side, and the reception signal Vr is received on the reception coupler side.

Figure 5B:
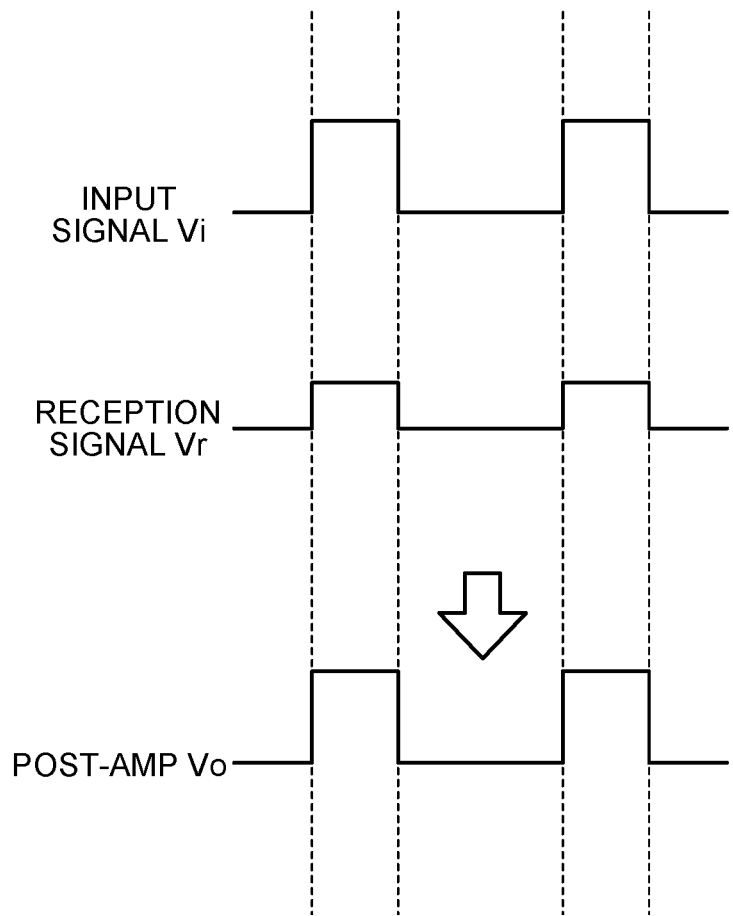
FIG. 5B is a chart illustrating another example of a waveform shaping process according to the first embodiment.

The shaping circuitry in FIG. 5A includes an amplifier (AMP) and also has relatively high impedance Z2. For example, the shaping circuitry in FIG. 5A is connected to the reception coupler and has a termination resistance that causes the waveform of the signal received by the reception coupler to be substantially square. In other words, as illustrated in FIG. 5B, when the input signal Vi has a square wave, the reception signal Vr is also substantially square. By performing an amplifying process, the amplifier AMP is capable of converting the reception signal Vr into a square wave exhibiting the waveform Vo depicted in FIG. 5B. FIG. 5B is a chart illustrating the present example of the waveform shaping process according to the first embodiment.

The shaping circuitry in FIG. 4A has an advantageous characteristic where resistance to external noise is higher than that of the shaping circuitry in FIG. 5A. The shaping circuitry in FIG. 5A has an advantageous characteristic where resistance to a gap fluctuation between the couplers is higher and the cost is lower than those of the shaping circuitry in FIG. 4A.

Figure 6:
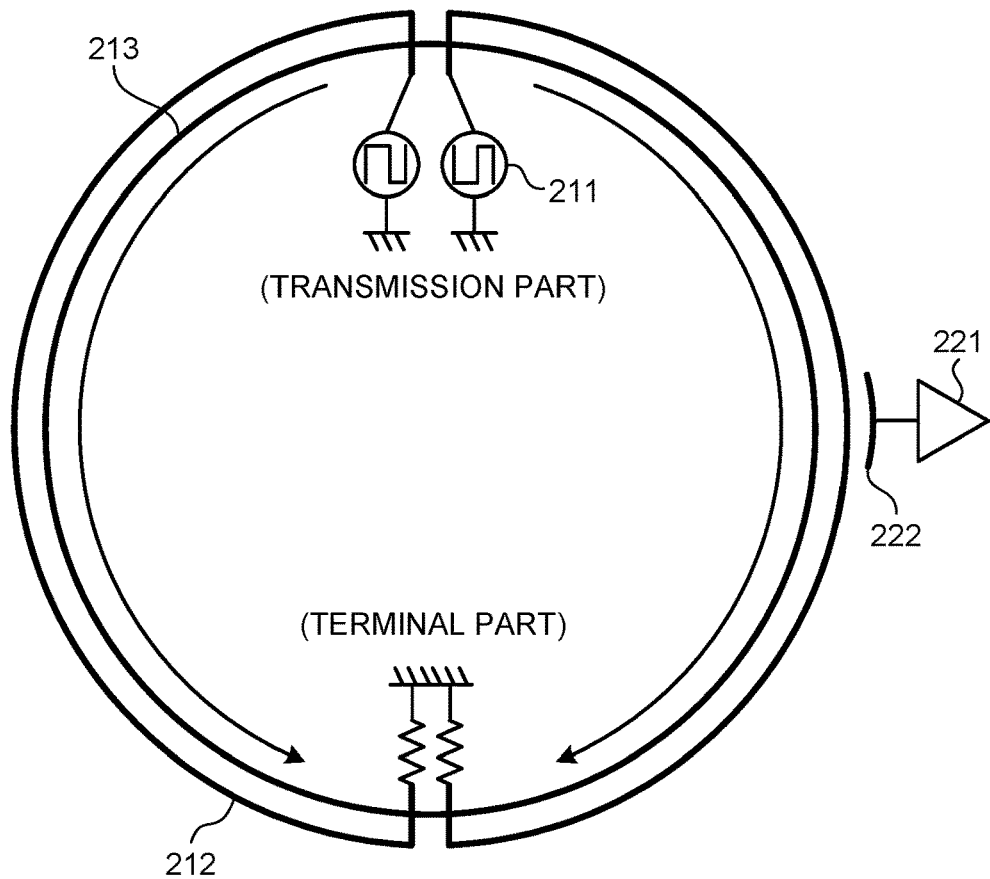
FIG. 6 is a diagram illustrating an example of the near field communication system according to the first embodiment.

Next, waveforms of the signal transmitted and received between the long couplers 212 and the short coupler 222 in the near field communication system 20 will be explained. In the following sections, an example will be explained in which the near field communication system 20 is structured as illustrated in FIG. 6. FIG. 6 is a diagram illustrating the example of the near field communication system 20 according to the first embodiment.

In FIG. 6, two long couplers 212 structure one circle. In other words, each of the long couplers 212 has a length corresponding to 180 degrees of the circumference. Further, each of the long couplers 212 is connected to the first signal processing unit 211. As indicated with the arrows in FIG. 6, the first signal processing unit 211 is configured to transmit a signal from a transmission part to a terminal part. In this situation, the transmission part is one end of each of the long couplers 212 connected to the first signal processing unit 211. The terminal part is the other end of each of the long couplers 212 opposite from the transmission part. The signal transmitted from the first signal processing unit 211 is received by the short coupler 222 in such a position in a long coupler 212 where the long coupler 212 is facing the short coupler 222.

In the present example, the positional relationship between the long couplers 212 and the short coupler 222 during a CT scan changes in conjunction with the rotation of the rotating part. In other words, the positional relationship between the long couplers 212 and the short coupler 222 may be the one illustrated in FIG. 6, may be another one in which the short coupler 222 is positioned at the transmission part, or may be yet another one in which the short coupler 222 is positioned at the terminal part. In other words, in conjunction with the rotation of the rotating part, the length of the signal transmission path from the first signal processing unit 211 to the second signal processing unit 221 varies. The length of the transmission path is the shortest when the short coupler 222 is positioned at the transmission part and is the longest when the short coupler 222 is positioned at the terminal part.

Figure 7:
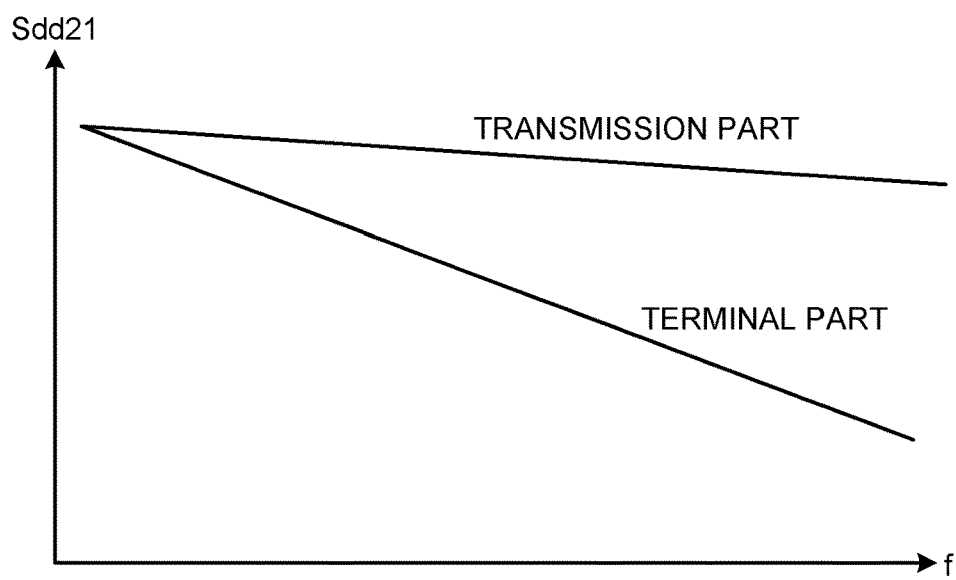
FIG. 7 is a drawing for explaining attenuation of a signal according to the first embodiment.

The transmitted signal attenuates depending on the length of the transmission path. Further, the degree of attenuation also varies depending on the frequency of the transmitted signal. The higher the frequency is, the more easily the signal is attenuated. Accordingly, it is possible to indicate degrees of attenuation of the transmitted signal as presented in FIG. 7. The horizontal axis in FIG. 7 expresses the frequency of the signal, whereas the vertical axis expresses a transmission loss (Sdd 21). In other words, when the short coupler 222 is positioned at the transmission part, the attenuation does not occur very much regardless of the frequency. In contrast, the attenuation occurs when the short coupler 222 is positioned at the terminal part. In particular, a signal having a higher frequency attenuates more significantly. In one example, when the short coupler 222 is positioned at the terminal part while the frequency of the signal is 5 GHz, attenuation to an extent of "−4.1 db (approximately 40%)" may occur. FIG. 7 is a drawing for explaining the attenuation of the signal according to the first embodiment.

Figure 8:
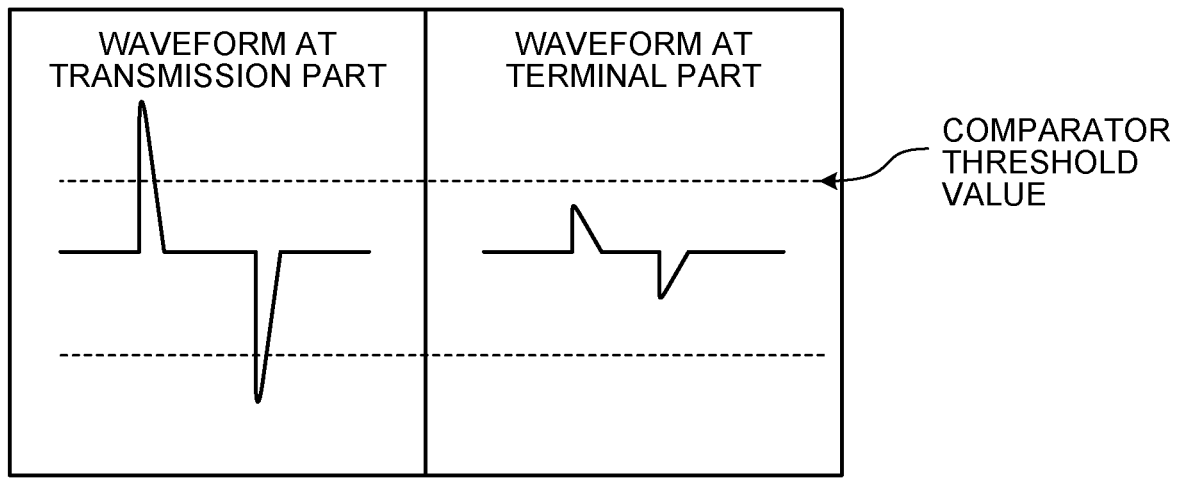
FIG. 8 is a drawing illustrating changes in waveforms depending on positions of the short coupler according to the first embodiment.
Figure 9:
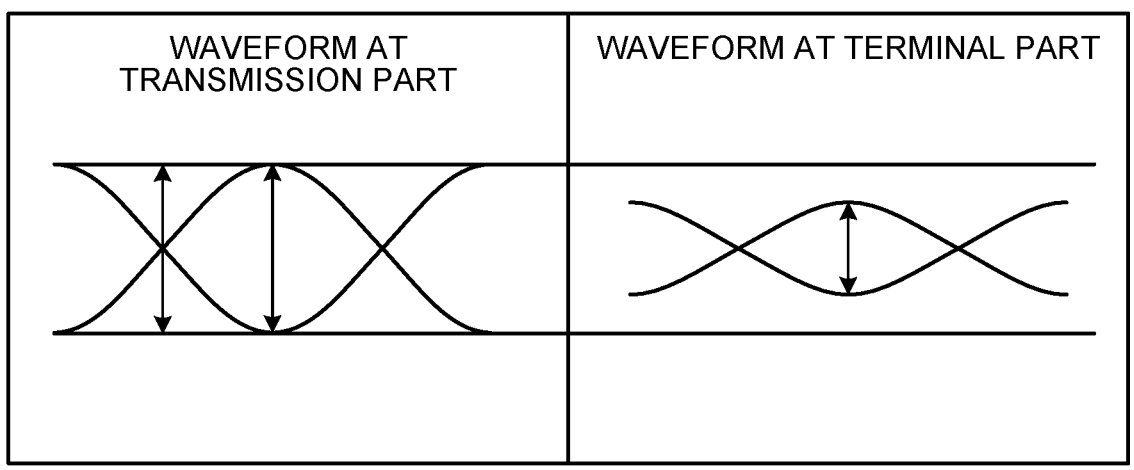
FIG. 9 is another drawing illustrating changes in the waveforms depending on the positions of the short coupler according to the first embodiment.

When the shaping circuitry in FIG. 4A or FIG. 5A is applied to the signal transmitted and received between the long couplers 212 and the short coupler 222, the waveform may change depending on the position of the short coupler 222 with respect to the long couplers 212. This phenomenon will be explained with reference to FIGS. 8 and 9. FIGS. 8 and 9 are drawings illustrating the changes in the waveforms depending on the position of the short coupler 222 according to the first embodiment.

For example, when the shaping circuitry in FIG. 4A is applied to signals transmitted from the long couplers 212 to the short coupler 222, a signal having a high frequency attenuates more significantly when the short coupler 222 is positioned at the terminal part than when the short coupler 222 is positioned at the transmission part. As a result, as illustrated in FIG. 8, the amplitude of the reception signal Vr having a waveform exhibiting a high frequency component becomes smaller and stops exceeding the comparator threshold value, which may cause a communication error. Further, the same is true when the shaping circuitry in FIG. 5A is applied to signals transmitted from the long couplers 212 to the short coupler 222. A signal having a high frequency attenuates more significantly when the short coupler 222 is positioned at the terminal part than when the short coupler 222 is positioned at the transmission part. As a result, as illustrated in FIG. 9, the opening ratio decreases, and thus a communication error may easily occur.

In relation to the attenuation of the signals at the time of being transmitted, techniques for performing an emphasis process and an equalization process are known. The emphasis process denotes processing a signal before being transmitted so that an output corresponding to the time when the signal value changes is stronger than an output corresponding to the time when the signal value does not change. More specifically, square waves have a waveform in which an output corresponding to the time when the signal value changes and an output corresponding to the time when the signal value does not change are constant. In contrast, in the emphasis process, the signal is transmitted after shaping the waveform in such a manner that an output corresponding to the time when the signal value changes is larger than an output corresponding to the time when the signal value does not change.

In other words, the emphasis process denotes performing, before the signal is transmitted, the process of emphasizing the high frequency component. Further, the emphasis process can be classified as: a de-emphasis process that decreases a low frequency component while keeping a high frequency component; and a pre-emphasis process that increases a high frequency component while keeping a low frequency component. At the time of transmission, because a high frequency component attenuates more significantly than a low frequency component does, when the emphasis process is performed with appropriate gain (an amplification factor or an amplification amount), the signal is received while the proportion of the high frequency component to the low frequency component is attenuated so as to realize a proportion close to the original proportion. In other words, when the emphasis process is performed with the appropriate gain, the signal is received while having a square wave in which the signal corresponding to the time when the signal value does not change and the signal corresponding to the time when the signal value changes are constant.

In contrast, the equalization process denotes supplementing an amount attenuated on a transmission path after a signal is received. For example, in the equalization process, a high frequency component of the received signal is increased. At the time when the signal is received, because the high frequency component is more significantly attenuated than a low frequency component, when the equalization process is performed with appropriate gain, the proportion of the high frequency component to the low frequency component is restored so as to realize a proportion close to the original proportion.

One idea is to correct the attenuation of the signal transmitted from the long couplers 212 to the short coupler 222 by performing the emphasis process or the equalization process. In other words, it is possible to address the attenuation of the high frequency component, by performing the emphasis process before the signal is transmitted or by performing the equalization process after the signal is received. For example, when a signal is to be transmitted from the long couplers 212 to the short coupler 222, the first signal processing unit 211 is able to transmit the signal after performing the emphasis process thereon. Also, the second signal processing unit 221 is able to perform the equalization process on the signal received by the short coupler 222.

Figure 10A:
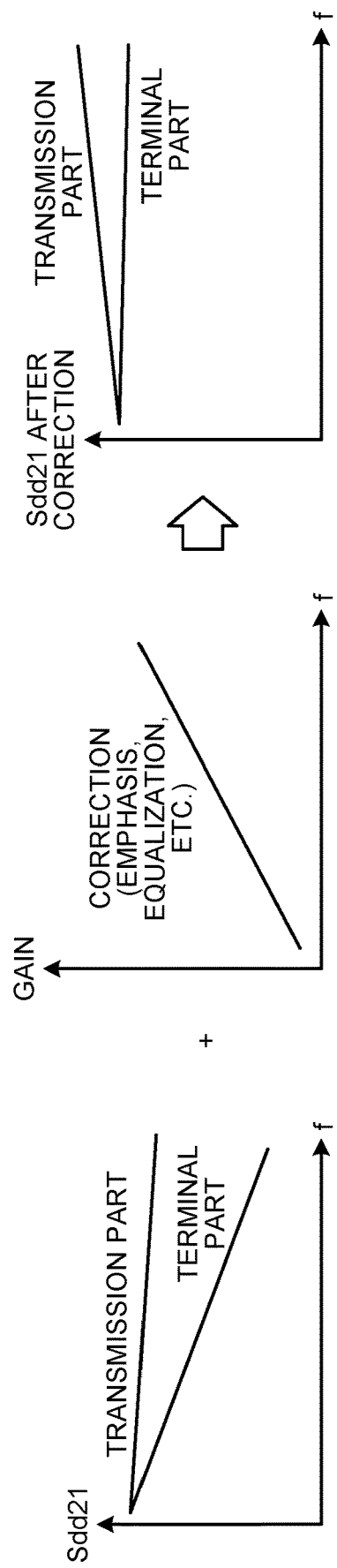
FIG. 10A is a drawing for explaining a signal correcting process according to the first embodiment.

More specifically, as illustrated in FIG. 10A, it is possible to perform a correcting process such as the emphasis process or the equalization process in such a manner that the gain increases as the frequency becomes higher. Even more specifically, in FIG. 10A, the gain is set for each of the various frequencies by using the attenuation amount corresponding to the time when the short coupler 222 is positioned at the terminal part as a reference. As a result, the signal transmitted while the short coupler 222 is positioned at the terminal part is corrected so that the attenuation amounts corresponding to the various frequencies are substantially constant. It should be noted, however, that in the present example the signal transmitted while the short coupler 222 is positioned at the transmission part is excessively amplified and is corrected so that the attenuation amount decreases as the frequency becomes higher. FIG. 10A is a drawing for explaining the signal correcting process according to the first embodiment.

For example, when the correcting process is performed by using the gain illustrated in FIG. 10A, the signal transmitted from the long couplers 212 to the short coupler 222 has waveforms as illustrated in FIG. 10B. In other words, the signal transmitted while the short coupler 222 is positioned at the terminal part is corrected so as to have a waveform close to a square wave. In contrast, the signal transmitted while the short coupler 222 is positioned at the transmission part is corrected so as to have a step-like waveform in which the high frequency component is larger than the low frequency component. FIG. 10B is a drawing illustrating the waveforms resulting from the correcting process according to the first embodiment.

For example, when the emphasis process is performed with the gain illustrated in FIG. 10A on a signal having a square wave, so that the signal is transmitted while the short coupler 222 is positioned at the terminal part, although the high frequency component is emphasized at the time of transmission, the high frequency component is appropriately attenuated during the transmission, so that the signal is received while having a square wave. In contrast, when the emphasis process is performed with the gain illustrated in FIG. 10A on a signal having a square wave, so that the signal is transmitted while the short coupler 222 is positioned at the transmission part, because the high frequency component emphasized at the time of transmission is not sufficiently attenuated, the signal is received while having a step-like waveform in which the high frequency component is emphasized.

In another example, when a signal having a square wave is transmitted without any correction, the high frequency component is more significantly attenuated than the low frequency component at the time of reception of the signal. Further, when the equalization process is performed with the gain illustrated in FIG. 10A on a signal transmitted while the short coupler 222 is positioned at the terminal part, the high frequency component is appropriately amplified so that the signal is shaped to have a square wave. In contrast, when the equalization process is performed with the gain illustrated in FIG. 10A on a signal transmitted while the short coupler 222 is positioned at the transmission part, the high frequency component is excessively amplified so that the signal is shaped to have a step-like waveform in which the high frequency component is emphasized.

Figure 10C:
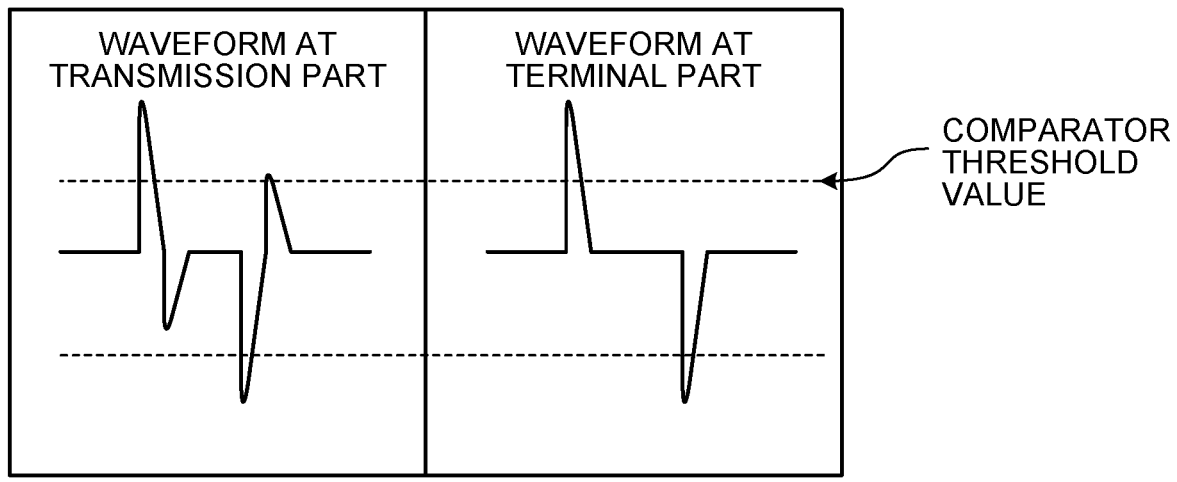
FIG. 10C is another drawing illustrating waveforms resulting from the correcting process according to the first embodiment.

When the shaping circuitry illustrated in FIG. 4A is applied to a signal having the waveforms illustrated in FIG. 10B, the reception signal Vr has waveforms as illustrated in FIG. 10C. In other words, the reception signal Vr corresponding to the time when the short coupler 222 is positioned at the terminal part is appropriately amplified and thus exceeds the comparator threshold value, and communication errors are thus prevented from occurring. In contrast, the reception signal Vr corresponding to the time when the short coupler 222 is positioned at the transmission part unfortunately contains a component derived from extra edges. In other words, due to the correcting process such as the emphasis process or the equalization process, the waveform exhibits the change which the original waveform (the waveform of the input signal Vi) did not have. The reception signal Vr thus exhibits the change as the edges, unfortunately. When the component derived from the extra edges exceeds the comparator threshold value, a communication error may occur. FIG. 10C is a drawing illustrating the waveforms resulting from the correcting process according to the first embodiment.

Figure 10D:
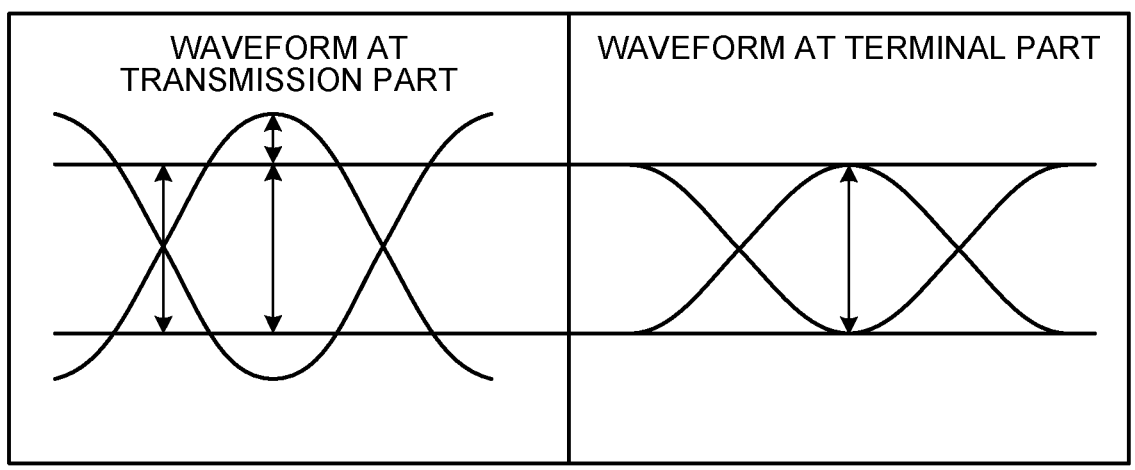
FIG. 10D is yet another drawing illustrating waveforms resulting from the correcting process according to the first embodiment.

Further, when the shaping circuitry illustrated in FIG. 5A is applied to a signal having the waveforms illustrated in FIG. 10B, the reception signal Vr has waveforms as illustrated in FIG. 10D. In other words, the reception signal Vr corresponding to the time when the short coupler 222 is positioned at the terminal part is appropriately amplified so that the opening degree increases, and communication errors are thus prevented from occurring. In contrast, the reception signal Vr corresponding to the time when the short coupler 222 is positioned at the transmission part unfortunately contains a useless high frequency component, which may be a cause of noise. FIG. 10D is a drawing illustrating the waveforms resulting from the correcting process according to the first embodiment.

To cope with these situations, the near field communication system 20 is configured to improve quality of the signal transmitted and received between the long couplers 212 and the short coupler 222 by performing the processes described below. More specifically, the near field communication system 20 is configured to vary the gain corresponding to each of various frequencies of the signal transmitted and received between the long couplers 212 and the short coupler 222, in accordance with the position of the short coupler 222 with respect to the long couplers 212.

For example, the first signal processing unit 211 is capable of performing the emphasis process on the signal transmitted from the long couplers 212 to the short coupler 222. In this situation, the first signal processing unit 211 is configured to vary the gain used in the emphasis process in correspondence with various positions of the short coupler 222 with respect to the long couplers 212 and in correspondence with the various frequencies of the signal. Further, the second signal processing unit 221 is capable of performing the equalization process on the signal received by the short coupler 222 from the long couplers 212. In this situation, the second signal processing unit 221 is configured to vary the gain used in the equalization process in correspondence with various positions of the short coupler 222 with respect to the long couplers 212 and in correspondence with the various frequencies of the signal.

The emphasis process and the equalization process may both be performed. In that situation, the first signal processing unit 211 and the second signal processing unit 221 are configured to vary a total gain value from both of the emphasis and equalization processes in correspondence with the various positions of the short coupler 222 with respect to the long couplers 212 and in correspondence with the various frequencies of the signal. In the following sections, when not being particularly distinguished from each other, the first signal processing unit 211 and the second signal processing unit 221 may simply be referred to as signal processing units. The signal processing units are configured to perform one or both of the emphasis process and the equalization process and to vary the gain for each of the various frequencies of the signal transmitted and received between the long couplers 212 and the short coupler 222, in accordance with the position of the short coupler 222 with respect to the long couplers 212.

Figure 11:
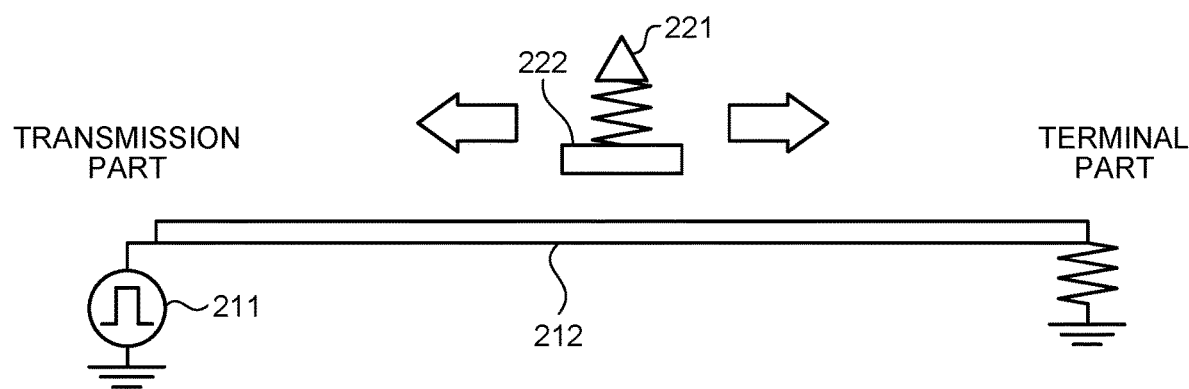
FIG. 11 is a conceptual drawing of a process performed by signal processing units according to the first embodiment.
Figure 12:
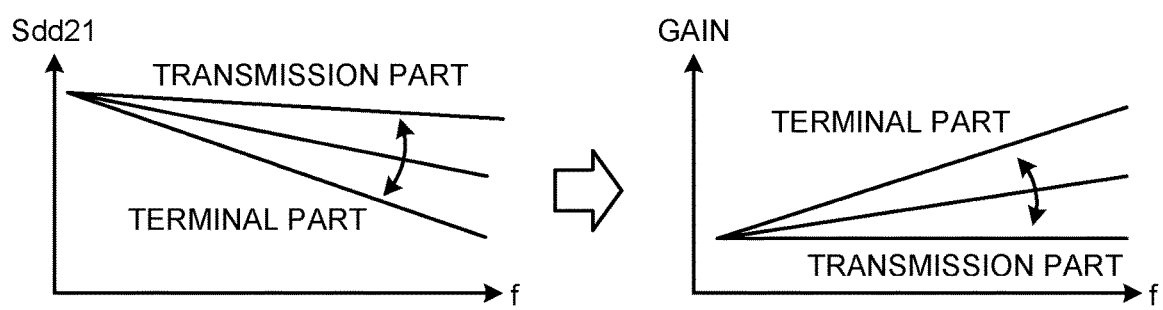
FIG. 12 is another conceptual drawing of the process performed by the signal processing units according to the first embodiment.

FIGS. 11 and 12 are conceptual drawings of a process performed by the signal processing units according to the first embodiment. To simplify the explanation, FIG. 11 depicts a long coupler 212 with a straight line. The signal transmitted by the first signal processing unit 211 travels through the long coupler 212 from the transmission part to the terminal part. In addition, the position of the short coupler 222 with respect to the long coupler 212 changes as indicated by the arrows in FIG. 11. In other words, because the long coupler 212 moves in conjunction with the rotation of the rotating part during a CT scan, the position of the short coupler 222 relative to the long coupler 212 changes as indicated by the arrows in FIG. 11.

More specifically, the position of the short coupler 222 with respect to the long coupler 212 changes from the transmission part to the terminal part. As illustrated in the left section of FIG. 12, the closer the short coupler 222 is positioned to the terminal part and the higher the frequency is, the more easily the signal is attenuated. Accordingly, the signal processing units are configured to vary the gain as illustrated in the right section of FIG. 12. In other words, the signal processing units are configured to vary the increase amounts of gain corresponding to increases in the frequency, in such a manner that the increase amount becomes larger as the short coupler 222 becomes closer to the terminal part.

Figure 13:
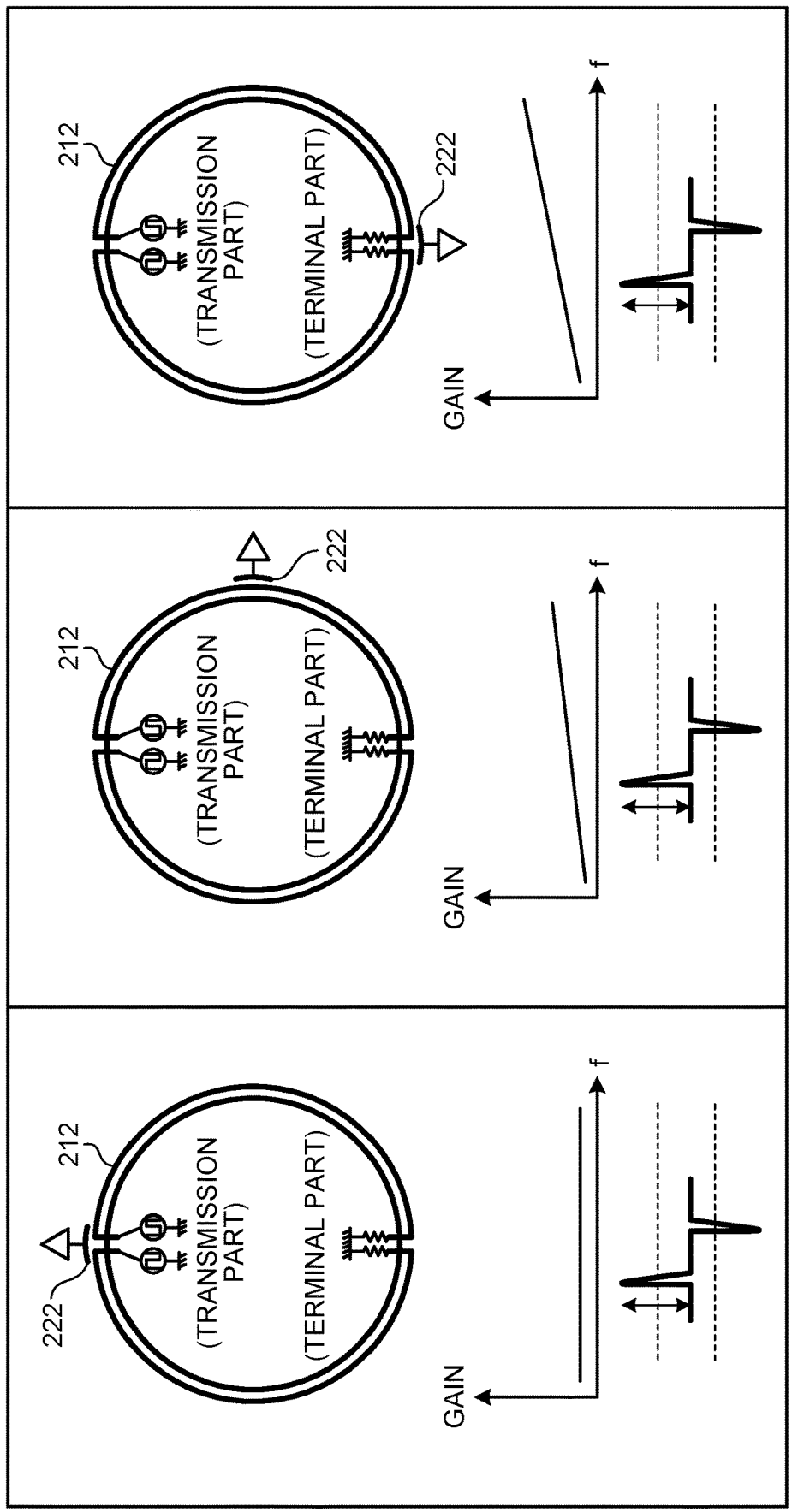
FIG. 13 is a drawing illustrating waveforms that have been corrected while gain is varied by the signal processing units according to the first embodiment, in a situation where the shaping circuitry in FIG. 4A is applied.

FIG. 13 is a drawing illustrating waveforms that have been corrected while the gain is varied by the signal processing units according to the first embodiment, in the situation where the shaping circuitry in FIG. 4A is applied. For instance, in the example in FIG. 13, the fixed part includes the shaping circuitry, while the shaping circuitry is connected to the short coupler 222 and has a termination resistance of approximately 100Ω.

For example, as illustrated in the left section of FIG. 13, when the short coupler 222 is positioned at the transmission part, the signal processing units are configured to perform the correcting process such as emphasis process and/or the equalization process, while keeping the gain corresponding to the various frequencies substantially constant. As another example, as illustrated in the middle section of FIG. 13, when the short coupler 222 is positioned between the transmission part and the terminal part, the signal processing units are configured to perform the correcting process so that the gain increases as the frequency becomes higher. As yet another example, as illustrated in the right section of FIG. 13, when the short coupler 222 is positioned at the terminal part, the signal processing units are configured to perform the correcting process by further increasing the increase amounts of gain corresponding to the increases in the frequency.

As illustrated in the left section of FIG. 13, the reception signal Vr corresponding to the time when the short coupler 222 is positioned at the transmission part contains no component derived from the extra edges. In other words, by taking it into consideration that the high frequency component is not easily attenuated when the short coupler 222 is positioned at the transmission part because the transmission path is shorter, the signal processing units are able to prevent the reception signal Vr from containing the component derived from the extra edges as illustrated in FIG. 10C by setting the gain to lower levels. Further, as illustrated in the right section of FIG. 13, the reception signal Vr corresponding to the time when the short coupler 222 is positioned at the terminal part is appropriately amplified and thus exceeds the comparator threshold value. In other words, by taking it into consideration that the high frequency component is easily attenuated when the short coupler 222 is positioned at the terminal part because the transmission path is longer, the signal processing units are able to avoid the situation where the reception signal Vr stops exceeding the comparator threshold value as illustrated in FIG. 8, by setting the gain to higher levels. As explained herein, when the shaping circuitry in FIG. 4A is applied, the signal processing units are able to improve the quality of the wireless communication based on the electromagnetic field coupling, by preventing the occurrence of communication errors, regardless of the position of the short coupler 222 with respect to the long couplers 212 and the frequency of the signal.

Figure 14:
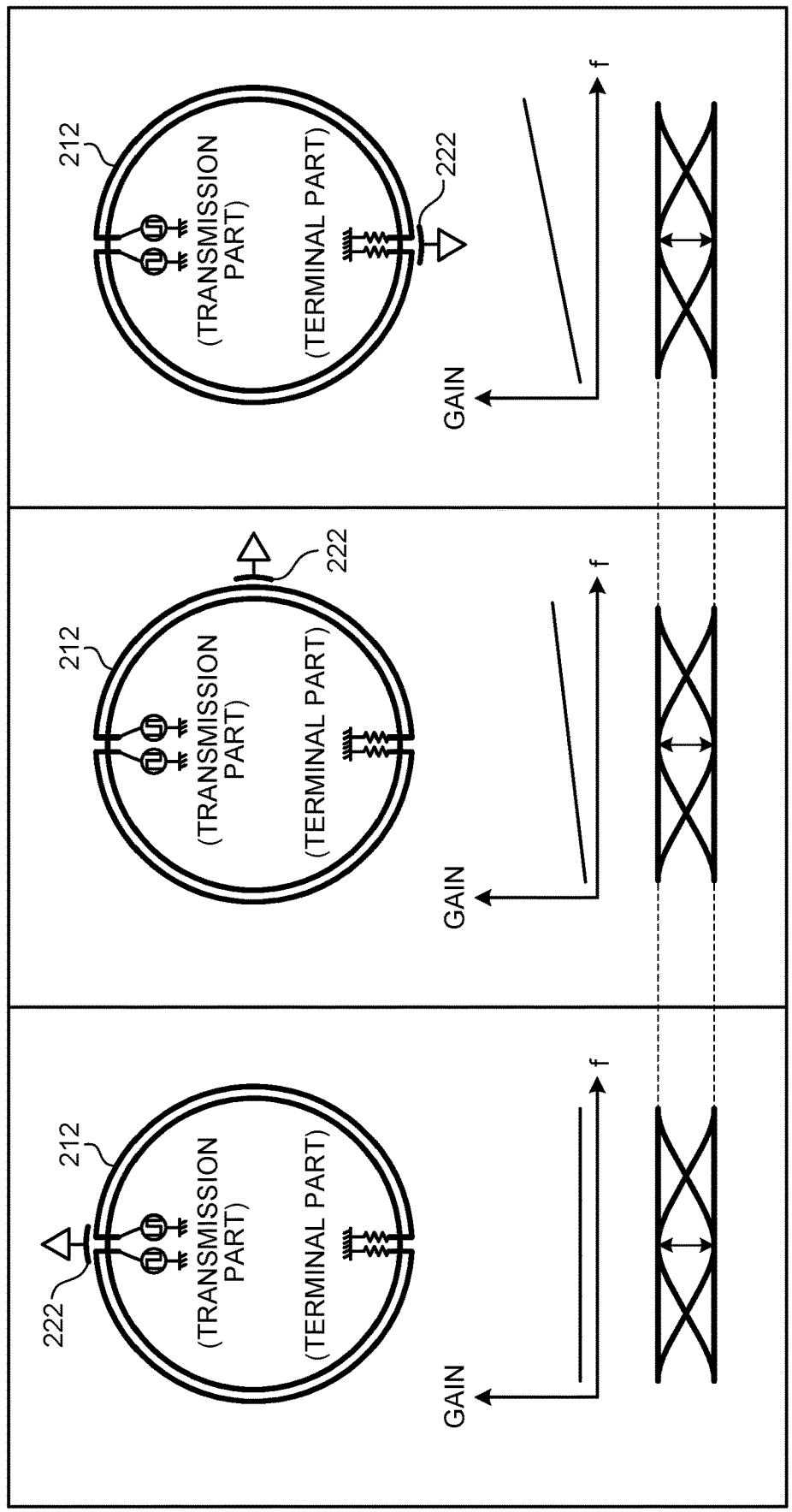
FIG. 14 is a drawing illustrating waveforms that have been corrected while gain is varied by the signal processing units according to the first embodiment, in a situation where the shaping circuitry in FIG. 5A is applied.

FIG. 14 is a drawing illustrating waveforms that have been corrected while the gain is varied by the signal processing units according to the first embodiment, in the situation where the shaping circuitry in FIG. 5A is applied. For instance, in the example in FIG. 14, the fixed part includes the shaping circuitry, while the shaping circuitry is connected to the short coupler 222 and has a termination resistance that causes the waveform of the signal received by the short coupler 222 to be substantially square.

For example, as illustrated in the left section of FIG. 14, when the short coupler 222 is positioned at the transmission part, the signal processing units are configured to perform the correcting process such as the emphasis process and/or the equalization process, while keeping the gain corresponding to the various frequencies substantially constant. As another example, as illustrated in the middle section of FIG. 14, when the short coupler 222 is positioned between the transmission part and the terminal part, the signal processing units are configured to perform the correcting process so that the gain increases as the frequency becomes higher. As yet another example, as illustrated in the right section of FIG. 14, when the short coupler 222 is positioned at the terminal part, the signal processing units are configured to perform the correcting process by further increasing the increase amounts of gain corresponding to the increases in the frequency.

As illustrated in the left section of FIG. 14, the reception signal Vr corresponding to the time when the short coupler 222 is positioned at the transmission part has a waveform having an appropriate opening ratio. In other words, by taking it into consideration that the high frequency component is not easily attenuated when the short coupler 222 is positioned at the transmission part because the transmission path is shorter, the signal processing units are able to prevent the reception signal Vr from containing the useless high frequency component as illustrated in FIG. 10D, by setting the gain to lower levels. Further, as illustrated in the right section of FIG. 14, the reception signal Vr corresponding to the time when the short coupler 222 is positioned at the terminal part is appropriately amplified. In other words, by taking it into consideration that the high frequency component is easily attenuated when the short coupler 222 is positioned at the terminal part because the transmission path is longer, the signal processing units are able to prevent the opening ratio of the reception signal Vr from decreasing as illustrated in FIG. 9, by setting the gain to higher levels. As explained herein, when the shaping circuitry in FIG. 5A is applied, the signal processing units are able to improve the quality of the wireless communication based on the electromagnetic field coupling, by preventing the occurrence of communication errors, regardless of the position of the short coupler 222 with respect to the long couplers 212 and the frequency of the signal.

Figure 15:
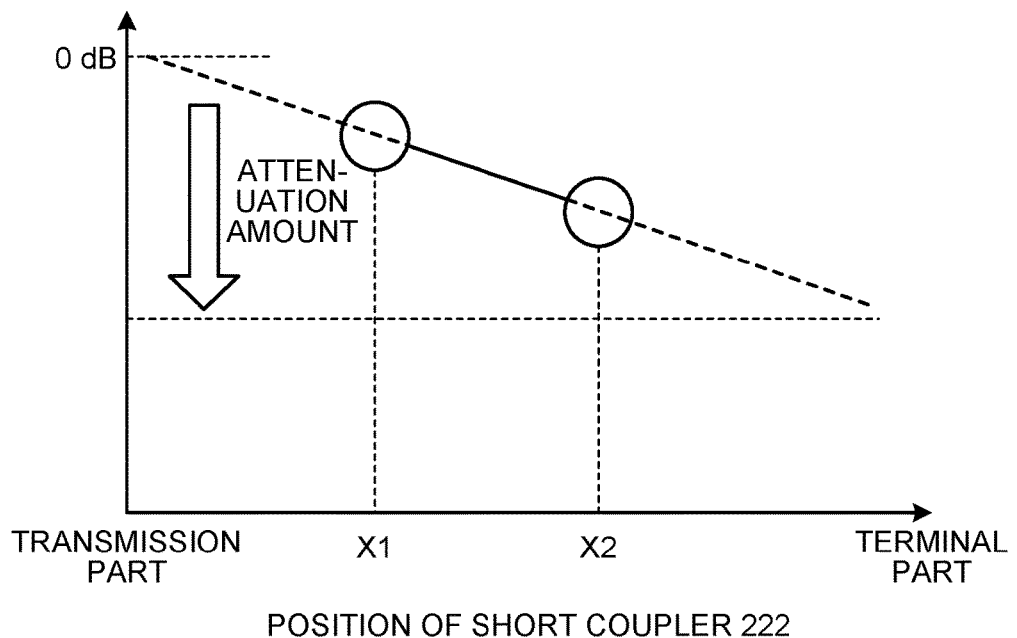
FIG. 15 is a drawing for explaining an example of a gain setting method according to the first embodiment.

As for the gain setting processes performed by the signal processing units described above, the gain may be set on the basis of a result of measuring an attenuation amount for each of the various frequencies of the signal. In the following sections, this process will be explained with reference to FIG. 15. FIG. 15 is a drawing for explaining an example of the gain setting method according to the first embodiment.

For example, when the short coupler 222 is positioned at a position X1 and a position X2 in FIG. 15, the first signal processing unit 211 is configured to transmit a training-purpose signal. In this situation, the position X1 and the position X2 are arbitrary two points between the transmission part and the terminal part. When the short coupler 222 is positioned at the terminal part, there is a possibility that an error may occur due to the mechanical structure. Accordingly, it is desirable when the position X1 and the position X2 are each a position different from the terminal part. Further, it is desirable when the position X1 and the position X2 have a certain distance therebetween. For example, when the position X1 and the position X2 may be set so as to divide the transmission path from the transmission part to the terminal part, into three equal sections. Further, the training-purpose signal is a broadband signal of which the signal in each band is known.

The training-purpose signal transmitted by the first signal processing unit 211 travels through the long coupler 212 and, after going through the wireless communication between the long coupler 212 and the short coupler 222 based on the electromagnetic field coupling, is received by the second signal processing unit 221. Further, it is possible to measure the attenuation amount for each of the various frequencies, by comparing the signal transmitted by the first signal processing unit 211 and the signal received by the second signal processing unit 221. In this situation, the attenuation amounts may be measured by the first signal processing unit 211, may be measured by the second signal processing unit 221, or may be measured by another device capable of communicating with the near field communication system 20. In the following sections, an example will be explained in which the processing circuitry 44 included in the console 40 is configured to measure the attenuation amounts.

For example, with respect to each of the positions X1 and X2, the processing circuitry 44 is configured to obtain values (hereinafter, "first signal values") corresponding to various frequencies of the training-purpose signal transmitted by the first signal processing unit 211 and values (hereinafter, "second signal values") corresponding to various frequencies of the signal received by the second signal processing unit 221. Further, the processing circuitry 44 is able to calculate the attenuation amount corresponding to each of the positions of the short coupler 222 by calculating, with respect to each of the positions X1 and X2, a ratio of the second signal value to the first signal value.

It is possible to measure the attenuation amounts corresponding to the position X1 and the position X2, for example, when the X-ray CT apparatus 1 is shipped from the factory, is installed in a hospital, or undergoes regular maintenance. As another example, the attenuation amounts may be measured when the X-ray CT apparatus 1 is put to use (e.g., when the power is turned on or turned off). As yet another example, the attenuation amounts may be measured according to an instruction from the user such as a medical doctor or a service person who performs the maintenance thereon. Because the attenuation amount measuring process is a type of calibration process, the precision level thereof may improve when being performed more frequently. However, because it is not possible to use the apparatus while the attenuation amounts are measured, it is desirable to perform the measuring process with appropriate frequency.

Further, although FIG. 15 illustrates the example in which the measuring process is performed at the two points (i.e., the position X1 and the position X2), the precision level of the calibration will improve when the measuring process is performed in a larger number of positions. For example, due to an error at the time of manufacture or aging over years, there may be variance in the size of the gap between the long couplers 212 and the short coupler 222 among different positions such as the position X1 and the position X2. Accordingly, there may be an impact on the measurement result of the attenuation amounts. To cope with this situation, by increasing the number of positions in which the measuring process is performed, it is possible to reduce the impact on the measurement result because the sizes of the gap are averaged. However, because the measuring time will become longer when the measuring process is performed in a larger number of positions, it is desirable to adjust the number of positions for the measuring process according to how much time can be spared for the calibration. For example, it is a good idea to perform the measuring process in a larger number of positions at the time of factory shipment and to perform the measuring process in a smaller number of positions while the X-ray CT apparatus 1 is in use.

The attenuation amounts corresponding to the positions of the short coupler 222 can be approximated to a straight line, as indicated with the dotted line in FIG. 15. Accordingly, the processing circuitry 44 is able to estimate an attenuation amount corresponding to the time when the short coupler 222 is positioned at the terminal part. The estimated result is transmitted to the signal processing units. For example, when the emphasis process and the equalization process are both performed, the processing circuitry 44 is configured to transmit the estimated result to the first signal processing unit 211 and the second signal processing unit 221.

When the CT scan is performed so that the wireless communication is performed between the long couplers 212 and the short coupler 222, the signal processing units are able to vary the gain for each of the various frequencies of the signal, on the basis of the estimated result of the attenuation amount corresponding to the time when the short coupler 222 is positioned at the terminal part. For example, on the basis of the estimated result of the attenuation amount, the first signal processing unit 211 is configured to determine a setting value for the signal level in the emphasis process. Further, on the basis of the estimated result of the attenuation amount, the second signal processing unit 221 is configured to set a filter characteristic in the equalization process.

As explained above, according to the first embodiment, the near field communication system 20 includes: the long couplers 212 included in the rotating part; the short coupler 222 included in the fixed part and configured to perform the wireless communication based on the electromagnetic field coupling, with the long couplers 212; and the signal processing units. The signal processing units are configured to vary the gain for each of the various frequencies of the signal transmitted and received between the long couplers 212 and the short coupler 222, in accordance with the position of the short coupler 222 with respect to the long couplers 212. Accordingly, the near field communication system 20 according to the first embodiment is able to improve the quality of the wireless communication based on the electromagnetic field coupling.

In other words, as illustrated in FIGS. 8 and 9, when the wireless communication based on the electromagnetic field coupling is performed between the long couplers 212 and the short coupler 222, a communication error might occur due to the changes in the length of the transmission path, in some situations. Further, as illustrated in FIGS. 10A to 10D, even when an attempt is made to correct the attenuation on the transmission path by performing the emphasis process and/or the equalization process, a communication error due to the correction might occur in some situations. In contrast, the near field communication system 20 according to the first embodiment is configured to vary the gain in accordance with the position of the short coupler 222 with respect to the long couplers 212. Consequently, it is possible to improve the quality of the wireless communication based on the electromagnetic field coupling, by preventing the occurrence of communication errors, regardless of the position of the short coupler 222 with respect to the long couplers 212 and the frequency of the signal.

Further, in the near field communication system 20 according to the first embodiment is able to improve the quality of the wireless communication based on the electromagnetic field coupling, both when the shaping circuitry illustrated in FIG. 4A is used and when the shaping circuitry illustrated in FIG. 5A is used. In other words, when the shaping circuitry in FIG. 4A is used, the near field communication system 20 according to the first embodiment does not have the occurrence of a signal caused by the extra edges such as that illustrated in FIG. 10C and is thus able to reduce radiation noise. Further, when the shaping circuitry in FIG. 5A is used, the near field communication system 20 according to the first embodiment does not have the occurrence of a useless high frequency component such as that illustrated in FIG. 10D and is thus able to reduce radiation noise. Consequently, the near field communication system 20 is able to select and use an arbitrary shaping circuitry in accordance with the advantageous characteristics of each of the shaping circuitry.

Further, as the X-ray detector 12, the X-ray CT apparatus 1 may include a detector 12a based on a photon counting method by which light beams derived from the X-rays that have passed through the patient P are individually counted. Every time an X-ray photon becomes incident thereto, the detector 12a is configured to output a signal that makes it possible to measure an energy value of the X-ray photon. Further, the DAS 18 is configured to discriminate individual signals output from the detector 12a and to acquire, for each of various phases of the X-ray tube 11 (X-ray tube phases), count information including incident positions (detection positions) of the X-ray photons and energy values of the X-ray photons. In other words, as the projection data, the DAS 18 is configured to acquire the count information including energy information of the X-ray photons.

The near field communication system 20 is also capable of transmitting the count information acquired by using the detector 12a, from the rotating part to the fixed part in a similar manner. The count information may have a larger data size than the projection data acquired when the photon counting method is not used. By preventing the occurrence of communication errors, the near field communication system 20 is able to have the count information wirelessly transmitted efficiently.

In the first embodiment described above, the example was explained in which the signal is transmitted from the long couplers 212 to the short coupler 222. In contrast, as a second embodiment, an example will be explained in which a signal is transmitted from the short coupler 222 to the long couplers 212. In other words, in the first embodiment, the example was explained in which the communication is performed in a downlink direction from the rotating part including the X-ray detector 12 and the like to the fixed part. In contrast, in the second embodiment, the example will be explained in which the communication is performed in an uplink direction from the fixed part to the rotating part. In the following sections, some of the elements that were explained in the first embodiment will be referred to by using the same reference characters used in FIGS. 1 to 15, and the explanations thereof will be omitted.

Even when the communication is performed in the uplink direction, the fact that the length of the transmission path changes depending on the position of the short coupler 222 with respect to the long couplers 212 and the characteristic where the high frequency component is easily attenuated are the same as when the communication is performed in the downlink direction. Accordingly, when a signal is transmitted without performing a correcting process such as the emphasis process and/or the equalization process, a communication error might occur similarly to the examples in FIGS. 8 and 9. Further, when an attempt is made to correct the attenuation on the transmission path by performing the emphasis process and/or the equalization process, a communication error due to the correction might occur, similarly to the examples in FIGS. 10A to 10D. In contrast, the near field communication system 20 according to the second embodiment is configured to improve quality of the communication in the uplink direction, by varying the gain for each of the various frequencies of the signal transmitted from the short coupler 222 to the long couplers 212, in accordance with the position of the short coupler 222 with respect to the long couplers 212.

Figure 16:
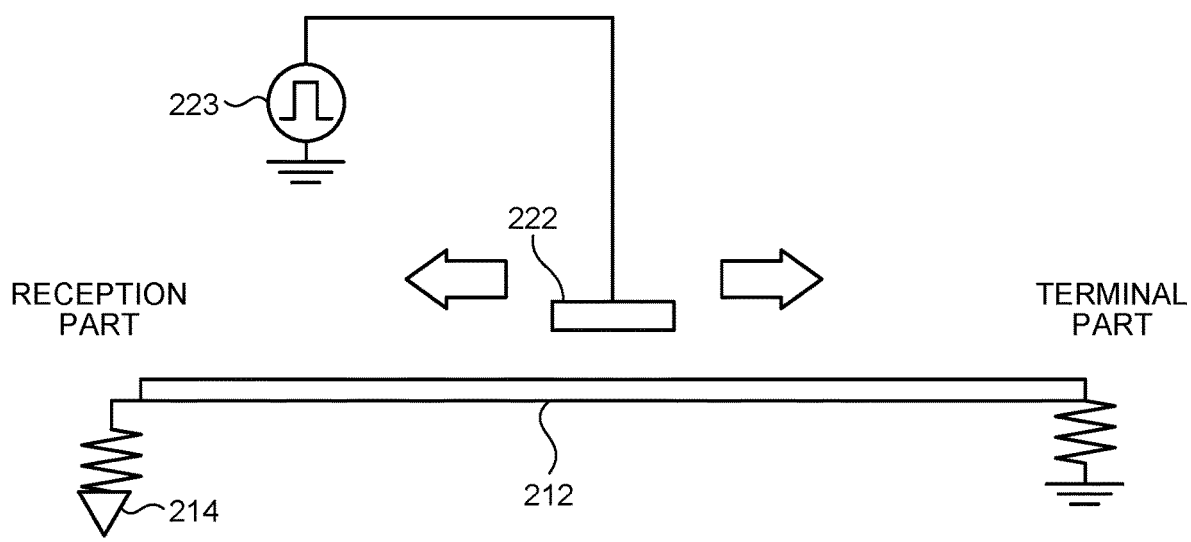
FIG. 16 is a diagram illustrating an example of a near field communication system 20 according to a second embodiment.

FIG. 16 is a diagram illustrating an example of the near field communication system 20 according to the second embodiment. For example, the near field communication system 20 includes a first signal processing unit 214 in place of the first signal processing unit 211 and a second signal processing unit 223 in place of the second signal processing unit 221. The second signal processing unit 223 is configured to transmit a signal toward the short coupler 222. The signal transmitted from the second signal processing unit 223 is received by a long coupler 212 in such a position in the long coupler 212 where the long coupler 212 is facing the short coupler 222. The signal received by the long coupler 212 travels up to a reception part, which is one end of the long coupler 212 and is received by the first signal processing unit 214. In this situation, examples of the signal transmitted from the second signal processing unit 223 include, for instance, control information for the X-ray tube 11 or the X-ray detector 12.

FIG. 17 is a drawing illustrating waveforms that have been corrected while gain is varied by signal processing units according to the second embodiment, in the situation where the shaping circuitry in FIG. 4A is applied. For instance, in the example in FIG. 17, the rotating part includes the shaping circuitry, while the shaping circuitry is connected to the long couplers 212 and has a termination resistance of approximately 100Ω.

For example, as illustrated in the left section of FIG. 17, when the short coupler 222 is positioned at the reception part, the signal processing units are configured to perform the correcting process such as the emphasis process and/or the equalization process while keeping the gain corresponding to the various frequencies substantially constant. As another example, as illustrated in the middle section of FIG. 17, when the short coupler 222 is positioned between the reception part and the terminal part, the signal processing units are configured to perform the correcting process so that the gain increases as the frequency becomes higher. As yet another example, as illustrated in the right section of FIG. 17, when the short coupler 222 is positioned at the terminal part, the signal processing units are configured to perform the correcting process by further increasing the increase amounts of gain corresponding to the increases in the frequency.

As illustrated in the left section of FIG. 17, the reception signal Vr corresponding to the time when the short coupler 222 is positioned at the reception part contains no component derived from the extra edges. In other words, by taking it into consideration that the high frequency component is not easily attenuated when the short coupler 222 is positioned at the reception part because the transmission path is shorter, the signal processing units are able to prevent the reception signal Vr from containing the component derived from the extra edges as illustrated in FIG. 10C, by setting the gain to lower levels. Further, as illustrated in the right section of FIG. 17, the reception signal Vr corresponding to the time when the short coupler 222 is positioned at the terminal part is appropriately amplified and thus exceeds the comparator threshold value. In other words, by taking it into consideration that the high frequency component is easily attenuated when the short coupler 222 is positioned at the terminal part because the transmission path is longer, the signal processing units are able to avoid the situation where the reception signal Vr stops exceeding the comparator threshold value as illustrated in FIG. 8, by setting the gain to higher levels. As explained herein, when the shaping circuitry in FIG. 4A is applied to the communication in the uplink direction, the signal processing units are able to improve the quality of the wireless communication based on the electromagnetic field coupling, by preventing the occurrence of communication errors, regardless of the position of the short coupler 222 with respect to the long couplers 212 and the frequency of the signal.

Further, although not illustrated, the present disclosure is similarly applicable to the situation where the shaping circuitry in FIG. 5A is applied to the communication in the uplink direction. Further, the near field communication system 20 may perform both the communication in the downlink direction and the communication in the uplink direction. In that situation, the rotating-part side communication unit 21 includes both the first signal processing unit and the first signal processing unit 214, whereas the fixed-part side communication unit 22 includes both the second signal processing unit 221 and the second signal processing unit 223.

Further, in the embodiments described above, the example was explained in which the two long couplers 212 form the one circle; however, the quantity of the long couplers 212 may arbitrarily be changed. For example, one circle may be formed by four long couplers 212 each having a length corresponding to 90 degrees. Alternatively, one circle may be formed by one long coupler 212 having a length corresponding to 360 degrees. The larger the quantity of the long couplers 212 is, the less easily the signal is attenuated because the transmission path becomes shorter. On the contrary, the smaller the quantity of the long couplers 212 is, the simpler is the structure of the device, which reduces manufacturing costs and burdens in the maintenance. Further, in the embodiments described above, the example was explained in which the long couplers 212 are provided on the rotating part side, whereas the short coupler 222 is provided on the fixed part side; however, the present disclosure is similarly applicable to the situation where the short coupler is provided on the rotating part side, whereas the long couplers are provided on the fixed part side.

The term "processor" used in the above explanations denotes, for example, a CPU, a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). When the processor is a CPU, for example, the processor is configured to realize the functions by reading and executing the programs saved in the storage circuit. In contrast, when the processor is an ASIC, for example, instead of having the programs saved in the storage circuit, the functions are directly incorporated in the circuit of the processor as a logic circuit. Further, the processors of the present embodiments do not each necessarily have to be structured as a single circuit. It is also acceptable to structure one processor by combining together a plurality of independent circuits so as to realize the functions thereof. Further, it is also acceptable to integrate two or more of the constituent elements illustrated in the drawings into one processor so as to realize the functions thereof.

Further, with reference to FIG. 1, the example was explained in which the single memory (i.e., the memory 41) has stored therein the programs corresponding to the processing functions of the processing circuitry 44; however, possible embodiments are not limited to this example. For instance, it is also acceptable to provide a plurality of memories 41 in a distributed manner, so that the processing circuitry 44 reads a corresponding program from each of the individual memories 41. Further, instead of having the programs saved in the memory 41, it is also acceptable to directly incorporate the programs in the circuits of one or more processors. In that situation, the one or more processors are configured to realize the functions by reading and executing the programs incorporated in the circuits thereof.

The constituent elements of the apparatuses and devices according to the above embodiments are based on functional concepts. Thus, it is not necessarily required to physically configure the constituent elements as indicated in the drawings. In other words, specific modes of distribution and integration of the apparatuses and devices are not limited to those illustrated in the drawings. It is acceptable to functionally or physically distribute or integrate all or a part of the apparatuses and devices in any arbitrary units, depending on various loads and the status of use. Further, all or an arbitrary part of the processing functions performed by the apparatuses and devices may be realized by a CPU and a program analyzed and executed by the CPU or may be realized as hardware using wired logic.

Further, it is possible to realize the near field communication controlling methods explained in the above embodiments, by causing a computer such as a personal computer or a workstation to execute a program prepared in advance. The program may be distributed via a network such as the Internet. Further, the program may be executed, as being recorded on a non-transitory computer-readable recording medium such as a hard disk, a flexible disk (FD), a Compact Disk Read-Only Memory (CD-ROM), a Magneto Optical (MO) disk, a Digital Versatile Disk (DVD), or the like and being read by a computer from the recording medium.

According to at least one aspect of the embodiments described above, it is possible to improve the quality of the wireless communication based on the electromagnetic field coupling.

What is claimed is:

1. A near field communication system comprising:
a long coupler provided for a first device;
a short coupler provided for a second device and configured to perform wireless communication based on electromagnetic field coupling, with the long coupler; and
signal processing circuitry configured to vary gain for each of various frequencies of a signal transmitted and received between the long coupler and the short coupler, in accordance with a position of the short coupler with respect to the long coupler.

2. The near field communication system according to claim 1, wherein the long coupler is configured to transmit the signal to the short coupler.

3. The near field communication system according to claim 2, wherein
the second device further includes shaping circuitry, and
the shaping circuitry is connected to the short coupler and has a termination resistance that causes a waveform of the signal received by the short coupler to be substantially square.

4. The near field communication system according to claim 2, wherein
the second device further includes shaping circuitry, and
the shaping circuitry is connected to the short coupler and has a termination resistance of approximately 100 Ω.

5. The near field communication system according to claim 2, comprising, as the signal processing circuitry, one or both of first signal processing circuitry provided for the first device and second signal processing circuitry provided for the second device, wherein
the first signal processing circuitry is configured to perform an emphasis process on the signal transmitted from the long coupler to the short coupler, and
the second signal processing circuitry is configured to perform an equalization process on the signal received by the short coupler from the long coupler.

6. The near field communication system according to claim 5, wherein the first signal processing circuitry is configured to vary the gain for each of the various frequencies of the signal, by performing the emphasis process in accordance with an attenuation amount for each of the various frequencies of the signal corresponding to the position of the short coupler with respect to the long coupler.

7. The near field communication system according to claim 5, wherein the second signal processing circuitry is configured to vary the gain for each of the various frequencies of the signal, by performing the equalization process in accordance with an attenuation amount for each of the various frequencies of the signal corresponding to the position of the short coupler with respect to the long coupler.

8. The near field communication system according to claim 1, wherein the short coupler is configured to transmit the signal to the long coupler.

9. The near field communication system according to claim 8, wherein
the first device further includes shaping circuitry, and
the shaping circuitry is connected to the long coupler and has a termination resistance of approximately 100 Ω.

10. The near field communication system according to claim 1, wherein the signal processing circuitry is configured to vary the gain for each of the various frequencies of the signal, on a basis of an estimated result of an attenuation amount for each of the various frequencies of the signal corresponding to a time when the short coupler is positioned at a terminal part of the long coupler, the estimated result being based on a measurement result of attenuation amounts corresponding to the various frequencies of the signal measured in multiple positions of the short coupler with respect to the long coupler.

11. The near field communication system according to claim 1, further comprising: a detecting unit configured to detect the position of the short coupler with respect to the long coupler.

12. The near field communication system according to claim 1, wherein
the first device is a rotating part configured to be rotatable around an examined subject in an X-ray Computed Tomography (CT) apparatus and includes an X-ray generating unit to generate X-rays and an X-ray detecting unit to detect the X-rays; and the second device is a fixed part of which, in the X-ray CT apparatus, a position is fixed with respect to the examined subject.

13. An X-ray Computed Tomography (CT) apparatus comprising:
    a first device that is configured to be rotatable around an examined subject and includes an X-ray generating unit to generate X-rays and an X-ray detecting unit to detect the X-rays;
    a second device of which a position with respect to the examined subject is fixed;
    a long coupler provided for the first device;
    a short coupler provided for the second device and configured to perform wireless communication based on electromagnetic field coupling, with the long coupler; and
    signal processing circuitry configured to vary gain for each of various frequencies of a signal transmitted and received between the long coupler and the short coupler, in accordance with a position of the short coupler with respect to the long coupler.

14. A near field communication controlling method for performing wireless communication based on electromagnetic field coupling between a long coupler provided for a first device and a short coupler provided for a second device, the near field communication controlling method comprising:
    varying gain for each of various frequencies of a signal transmitted and received between the long coupler and the short coupler, in accordance with a position of the short coupler with respect to the long coupler.

15. The near field communication controlling method according to claim 14, wherein the long coupler is configured to transmit the signal to the short coupler.

16. The near field communication controlling method according to claim 15, wherein first signal processing circuitry provided for the first device is configured to perform an emphasis process on the signal transmitted from the long coupler to the short coupler, and second signal processing circuitry provided for the second device is configured to perform an equalization process on the signal received by the short coupler from the long coupler.

17. The near field communication controlling method according to claim 16, wherein the first signal processing circuitry is configured to vary the gain for each of the various frequencies of the signal, by performing the emphasis process in accordance with an attenuation amount for each of the various frequencies of the signal corresponding to the position of the short coupler with respect to the long coupler.

18. The near field communication controlling method according to claim 16, wherein the second signal processing circuitry is configured to vary the gain for each of the various frequencies of the signal, by performing the equalization process in accordance with an attenuation amount for each of the various frequencies of the signal corresponding to the position of the short coupler with respect to the long coupler.

19. The near field communication controlling method according to claim 14, wherein the short coupler is configured to transmit the signal to the long coupler.

20. The near field communication controlling method according to claim 14, wherein the gain for each of the various frequencies of the signal is varied on a basis of an estimated result of an attenuation amount for each of the various frequencies of the signal corresponding to a time when the short coupler is positioned at a terminal part of the long coupler, the estimated result being based on a measurement result of attenuation amounts corresponding to the various frequencies of the signal measured in multiple positions of the short coupler with respect to the long coupler.

* * * * *